US007829548B2

(12) United States Patent  
Zhou et al.

(10) Patent No.: US 7,829,548 B2
(45) Date of Patent: Nov. 9, 2010

(54) COMPOUNDS USEFUL IN THE TREATMENT OF HIV

(75) Inventors: Xiao-Xiong Zhou, Huddinge (SE); Hong Zhang, Huddinge (SE)

(73) Assignee: Medivir AB, Huddinge (SE)

( * ) Notice: Subject to any disclaimer, the term of this patent is extended or adjusted under 35 U.S.C. 154(b) by 261 days.

(21) Appl. No.: 11/813,085

(22) PCT Filed: Dec. 28, 2005

(86) PCT No.: PCT/EP2005/057196

§ 371 (c)(1), (2), (4) Date: Dec. 19, 2007

(87) PCT Pub. No.: WO2006/070004

PCT Pub. Date: Jul. 6, 2006

(65) Prior Publication Data

US 2008/0176817 A1   Jul. 24, 2008

Related U.S. Application Data

(60) Provisional application No. 60/714,536, filed on Dec. 30, 2004.

(30) Foreign Application Priority Data

Jan. 6, 2005   (EP) .................................. 05100063

(51) Int. Cl.
*A01N 43/04* (2006.01)
*A61K 31/70* (2006.01)
(52) U.S. Cl. ............................. 514/49; 514/42; 514/43; 514/50; 514/51
(58) Field of Classification Search ........................ None
See application file for complete search history.

(56) References Cited

U.S. PATENT DOCUMENTS

| 5,473,063 A | 12/1995 | Classon |
| 5,612,319 A | 3/1997 | Oberg |

FOREIGN PATENT DOCUMENTS

| EP | 391411 A2 | 10/1990 |
| WO | WO 92/06102 | 4/1992 |
| WO | WO 95/32983 | 12/1995 |

OTHER PUBLICATIONS

Balzarini et al. AIDS Research and Human Retroviruses (2000), vol. 16, pp. 517-528.*
Naeger, L.K, et al., Comparison of nucleoside and nucleotide reverse transcriptase inhibitor removal by the adenosine triphosphate-dependent chain-terminator removal mechanism, Antiviral Therapy, (2001), vol. 6, p. 39.
Ohrui, H., et al., Syntheses of 4'-C-Ethynyl-B-D-arabino- and 4'-C-Ethynyl-2'-deoxy-B-D-ribo-pentofuranosylpyrimidines and—purines and evaluation of their aniti-HIV activity, J. Med. Chem., (2000), vol. 43, pp. 4516-4525.
Parikh, U., et al., A multi-nucleoside resistance mutation of low but increasing frequency, Antiviral Therapy, (2003), vol. 8, p. S152.
Parikh, U., et al., A multi-nucleoside resistance mutation of increasing prevalence exhibits bi-directional phenotypic antagonism with TAM, Conf. Retroviruses Opportunistic Infect., (2004), Feb. 8-11;11th:Abstract No. 54.
Reardon, J.E., Human Immunodeficiency virus reverse transcriptase, J. Biol. Chem., (1993), vol. 268, pp. 8743-8751.
Roberts, J.D., et al., The accuracy of reverse transcriptase from HIV-1, Science, (1998), vol. 242, pp. 1171-1173.
Sarafianos, S.G., et al., Structures of HIV-1 reverse transcriptase with pre- and post-translocation AZTMP-terminated DNA, EMBO J., (2002), vol. 21, pp. 6614-6624.
Sarafianos, S.G., et al., Trapping HIV-1 Reverse Transcriptase before and after translocation on DNA, J. Biol. Chem., (2003), vol. 278, pp. 16280-16288.
Sarafianos, S.G., et al., Designing anit-AIDS drugs targeting the major mechanism of HIV-1 RT resistance to nucleoside analog drugs, Intl. J. Biochem. & Cell Biology, (2004), vol. 36, pp. 1706-1715.
Sluis-Cremer, N., et al., Molecular mechanisms of HIV-1 resistance to nucleoside reverse transcriptase inhibitors (NRTIs), Cell. Mol. Life Sci., (2000), vol. 57, pp. 1408-1422.
St Clair, M.H., el al., Resistance to ddl and sensitivity to AZT induced by a mutating HIV-1 reverse transcriptase, Science, (1991), vol. 253, pp. 1557-1559.
Sturmer, M., et al., Correlation of phenotypic zidovudine resistance with mutational patters in the reverse transcriptase of human immunodeficiency virus type 1, Antimicrob. Agents Chemother., (2003), vol. 47, pp. 54-61.
Martin, J.L., et al., Mechanism of resistance of human immunodeficiency virus type 1 to 2',3'-dideoxyinosine, Proc. Natl. Acad. Sci. USA, (1993), vol. 90, pp. 6135-6139.
Martinez-Picado, J., et al., HIV-1 drug resistance assays in clinical management, AIDS Clinical Care, (1998), vol. 10, pp. 81-88.
Gait, M.J., et al., Progress in anti-HIV structure-based design, Trends in Biotechnology, (1995), vol. 13, pp. 430-438.
Mas, A., et al., Role of a dipeptide insertion between codons 69 and 70 of HIV-1 reverse transcriptase in the mechanism of AZT resistance, EMBO Jo., (2000), vol. 19, pp. 5752-5761.
Mauldin, S.C., et al., Synthesis and antiviral activity of prosrugs of the nucleoside 1-[2',3'-dideoxy-3'-C-(hydroxymethyl)-B-D-Erythropentofuranosyl] cytosine, Bioorg. Med Chem. Lett. (1998), vol. 6. pp. 577-585.
Melby, T., et al., Time to appearance of NRTI-associated mutation and response to subsequent therapy for patients on failing ABC/COM, (2001) 8th Conf. Retroviruses & Opportunistic Infections, Chicago Feb. 4-8, 2001, Abstract 448.
Mellors, J.W., et al., Mutation in retroviral genes associated with drug resistance, Int Antiviral News, (1996), vol. 4, pp. 95-97.

(Continued)

Primary Examiner—Patrick T Lewis
(74) Attorney, Agent, or Firm—Birch, Stewart, Kolasch and Birch, LLP

(57) ABSTRACT

There is provided inter alia use of 2',3'-dideoxy-3'-hydroxymethylcytidine or a prodrug or salt thereof in the manufacture of a medicament for the treatment of HIV infection wherein the reverse transcriptase of the HIV bears at least one mutation that allows an obligate chain terminating nucleoside- or nucleotide phosphate to be excised from the nascent DNA strand by ATP- or pyrophosphate-mediated excision.

20 Claims, 11 Drawing Sheets

OTHER PUBLICATIONS

Meyer, P.R., et al., Effects of dipeptide insertions between codons 69 and 70 of HIV type 1 reverse transcriptase on primer unblocking, deoxynucleoside triphosphate inhibition, and DNA chain elongation, J Virol, (2003), vol. 77, pp. 3871-3877.

Miller, V., et al., Dual resistance to zidovudine and lamivudine in patients treated with zidovudine-lamivudine combination therapy, J Inf Dis, (1998), vol. 177, pp. 1521-1532.

Miller, V., et al., HIV-1 reverse transcriptase (RT) genotype and susceptibility to RT inhibitors during abacavir monotherapy and combination therapy, AIDS, (2000), vol. 14, pp. 912-920.

Mitsuya, H., et al., Molecular targets for AIDS therapy, Science, (1990), vol. 249, pp. 1533-1544.

Montes, B., et al., Prevalence of the mutational pattern E55D/A and/or V118I in the reverse transcriptase (RT) gene of HIV-1 in relation to the treatment with nucleoside analogue RT inhibitors, J Med Virol, (2002), vol. 66, pp. 299-303.

Jacobo-Molina, A., et al., Crystal structure of HIV type 1 reverse transcriptase complexed with double-stranded DNA at 3.0 A resolution shows bent DNA, Proc. Natl. Acad. Sci. USA, (1993), vol. 90, pp. 6320-6324.

Kemp, S., et al., A novel polymorphism at codon 333 of HIV type 1 reverse transcriptase can facilitate dual resistance to zidovudine and L-2',3'-dideoxy-3'-thiacytidine, J Virol., (1998), vol. 72, pp. 5093-5098.

Kodama, E., et al., 4'-ethynyl nucleoside analogs, Antimicro. Agents Chemother., (2001), vol. 45, pp. 1539-1546.

Larder, B.A., et al., A family of insertion mutations between codons 67 and 70 of HIV type 1 reverse transcriptase confer multinucleoside analog resistance, Antimicro. Agents Chemother., (1999), vol. 43, pp. 1961-1967.

Lee, H., et al, Toxicity of nucleoside analogue used to treat AIDS and the selectivity of the mitochondrial DNA polymerase, Biochemistry, (2003), vol. 42, pp. 14711-14719.

Loveday, C., Nucleoside reverse transcriptase inhibitor resistance, JAIDS, (2001), vol. 26, pp. S10-S24.

Marcelin, A., et al., Thymidine analogue reverse transcriptase inhibitors resistance mutation profiles and association, J Med Virol, (2004), vol. 72, pp. 162-165.

Bottiger, D., et al., Prevention of $SIV_{sm}$ or HIV-2 infection in cynomolgus monkeys, AIDS, (1997), vol. 11, pp. 157-162.

Boyer, P.L., Effect of the 67 complex mutations in HIV type 1 reverse transcriptase on nucleoside analog excision, J Virology, (2004), vol. 78, pp. 9987-9997.

Chen, M.S., et al., Selective action of 4'-azidothymidine triphosphate on reverse transcriptase of HIV-1 and human DNA, Biochemistry, (1993), vol. 32, pp. 6002-6010.

Girouard, M., et al., Mutations E44D and V118I in the reverse trancriptase of HIV-1 play distinct mechanistic roles, J Biolog. Chem., (2003), vol. 278, pp. 34403-34410.

Imamichi, T., et al., Amino acid deletion at codon 67 and thr-to gly change and codon 69 of HIV-1 RT confer novel drug resistance profiles, J Virology, (2001), vol. 75, pp. 3988-3992.

Boyer, P.L., et al., Nucleoside analog resistance caused by insertions in the fingers of HIV-1 RT involves ATP-mediated excision, J Virology, (2002), vol. 76, pp. 9143-9151.

Larder, B.A., et al., Multiple mutations in HIV-1 RT confer high level resistance to zidovudine, Science, (1989), vol. 246, pp. 1155-1158.

Valer, L., et al., Predictors of selection of K65R: tenofovir use and lack of thymidine analogue mutations, AIDS, (2004), vol. 18, pp. 2094-2096.

Yahi, N., et al., Mutation patterns of the RT and protease genes in HIV type 1 infected patients undergoing combination therapy, J Clinical Microbio, (1998), vol. 37, pp. 4099-4106.

Office Action issued in Chinese Patent Application No. 200580048871.X - issued on Jul. 21, 2010.

* cited by examiner

COMPOUNDS USEFUL IN THE TREATMENT OF HIV

CROSS REFERENCE TO RELATED APPLICATIONS

This application is the U.S. National Stage of International Application No. PCT/EP2005/057196, filed Dec. 28, 2005, which claims priority to U.S. Provisional Application No. 60/714,536, filed Dec. 30, 2004 and European Patent Application No. 05100063.6, filed Jan. 6, 2005. All of the preceding applications are hereby incorporated by reference in their entirety.

FIELD OF THE INVENTION

This invention relates to methods and pharmaceutical compositions for the prophylaxis or treatment of a human immunodeficiency virus (HIV) which bears at least one well defined class of mutations in the reverse transcriptase (RT) gene that produces a primer rescue (excision) phenotype. These classes of mutations are associated with particular thymidine analogue mutations (TAMs) and are termed primer rescue-related mutations. The methods and pharmaceutical compositions of the invention employ the nucleoside 2',3'-dideoxy-3'-C-hydroxymethylcytidine or prodrugs releasing this nucleoside in vivo.

TECHNICAL BACKGROUND

Unlike other HIV antivirals, such as protease inhibitors or non-nucleoside reverse transcriptase inhibitors, nucleoside reverse transcriptase inhibitors (NRTI) are pharmacologically inactive in their administered form and require phosphorylation by host cellular kinases to produce the active triphosphate metabolite. This triphosphate form resembles the naturally occurring deoxynucleotide triphosphate substrates of the viral reverse transcriptase and competes for HIV-1 RT binding and incorporation into viral DNA.

All NRTIs approved for the treatment of HIV, and the vast majority of all other NRTIs proposed in the patent or academic literature, lack a 3'-hydroxy function on the ribose moiety of the nucleoside. Examples include zidovudine (AZT), stavudine (d4T), lamivudine (3TC), zalcitabine (ddC), abacavir (ABC), didanosine (ddI) and tenofovir (TNF) (the latter being typically administered as the disoproxil fumarate prodrug). Upon phosphorylation, such a nucleoside or nucleotide analogue is covalently bonded by the reverse transcriptase enzyme to the nascent DNA strand, but the lack of a 3'-hydroxyl function in the nucleoside or nucleotide prevents further attachment of additional nucleotides. These NRTIs therefore terminate viral DNA strand prolongation, thereby leading to inhibition of HIV replication (Mitsuya et al 1990, Jacob Molina et al 1993, Reardon 1993).

The cornerstone of all current antiretroviral therapies (ART) is the use of NRTIs. NRTIs, however, are only able to retard HIV propagation in the blood stream and to date have been unable to eradicate HIV from patients. HIV operates by inserting its DNA into latent host cells involved in human immunologic memory. This mode of infection implies that patients are forced to take HIV antivirals lifelong in order to prevent the HIV titre from bouncing back after therapy has ended.

In practice, however, the effective administration period of a particular HIV drug for a given patient is dramatically limited by the emergence of "escape mutants." An escape mutant is a virus that contains a discrete cluster of mutations that produces drug resistance and allows it to proliferate in the presence of the drug. Escape mutants arise in a patient due to the selective pressure of the particular antiviral(s) that the patient is taking. As a consequence, a drug's effective administration period is dependent on how quickly escape mutants arise and proliferate.

In countries consistently prescribing HIV antivirals it is becoming increasingly evident that the primary infection in new cases of HIV is often not with wild type HIV, but rather with a strain of HIV which is already partly or multiply resistant to the current antivirals. In other words, escape mutants which are generated in situ in infected patients can also be spread to naive patients by lateral or vertical transmission. This in turn means that even some patients who would otherwise be classified as treatment-naive are already infected with virus resistant to conventional first line therapies.

Multiple factors contribute to the selection of drug escape mutants including total HIV pool size, RT processivity and infidelity in viral genomic replication, viral fitness and multiple availabilities of target cells. By the late 1990s, evidence from long term use of combinations based on zidovudine (AZT) or stavudine (d4T) suggested that clusters of particular mutations in the RT were consistently generated. These mutation clusters are the prototype now known as Thymidine Analogue Mutations (TAMs). The presence of TAMs enhanced the likelihood of selecting further mutations and led to the development of more advanced NRTI resistance phenotypes that were not clearly within the family of thymidine analogues. Such phenotypes are now known as Nucleoside Analogue Mutation (NAM) and Multiple Drug Resistance (MDR) HIV.

Hypothesis for NRTI Resistance

AZT was the first antiretroviral to be widely used and not surprisingly was the first to generate escape mutants (Larder et al., 1989). However in view of the large number of mutations throughout the HIV genome in typical patient isolates it is not possible to produce the resistance phenotype in vitro using a recombinant RT enzyme bearing the particular TAM. As a consequence, the mechanisms through which TAMs confer resistance have not been straightforward to elucidate.

Various hypothetical models and theoretical predictions for the mechanism behind TAM resistance have been predicated on the involvement of nucleophilic attack by a pyrophosphate donor (Boyer et al, 2002 and Meyer et al, 2002). Presumably RT translocation theory is a key step in understanding the TAM associated resistance mechanism. This was, however, poorly understood until the end of 2002 because the RT pre- and post-translocation intermediates are transient and short-lived and not readily accessed experimentally.

The modern understanding of RT translocation theory holds that RT catalyzed DNA polymerization takes place in a detailed cascade fashion as illustrated in FIG. 3, which is adopted from Sarafianos et al (2003). These steps are 1) Binding of the DNA substrate by free enzyme E positions the 3'-primer end at the P-site (Primer site).
2) Binding of a dNTP close to the N-site (dNTP site) forms an "open" ternary complex.
3) A "closed" ternary complex is formed by enzyme conformational changes.
4) Phosphodiester bond formation between the 3'-OH primer terminus and the alpha phosphate of the dNTP is accompanied by release of pyrophosphate (PPi) to form the pre-translocated RT complex at the N-site.

5) Translocation of the primer terminus from the N-site to the P-site by forming a post-translocated complex which is a prerequisite for the next dNTP binding and continuation of DNA synthesis.

If a DNA chain terminator nucleoside (NRTI) triphosphate (typically a nucleoside analogue which lacks a 3'-hydroxy function on the deoxyribose moiety) is used, it mimics its natural dNTP counterpart and binds to RT. After the analogous chemical processing, the incorporated NRTI forms a pre-translocation complex at the N-site of polymerization. This terminates further DNA synthesis due to the lack of a 3'-hydroxyl primer on the NRTI's deoxyribose moiety.

In contrast, TAM-related RT mutations employ a different nucleotide incorporation mechanism compared to wild type RT. Specifically, the new mechanism results in the release (excision) of the NRTI incorporated at the primer terminus, abrogating the chain terminating activity of the NRTI. This new mechanism is dependent on the interplay between the accumulation of complexes in pre-translocated states (at the N-site) and the availability of ATP or pyrophosphate donors, which are often abundant at the site of infection, i.e. normal lymphocytes.

ATP or pyrophosphate does not normally participate in viral DNA-polymerization reactions, but the structure of a RT expressing a TAM-related resistant phenotype facilitates their entry into a site adjacent to a newly incorporated NRTI. The equilibrium between pre- and post-translocational kinetic species provides a mechanism to ensure free access of the primer terminus to the N-site and also allows simultaneous binding of the pyrophosphate donor ATP at the P-site after the incorporation of the NRTI chain terminator and the release of pyrophosphate. When this occurs, ATP (or pyrophosphate) attacks the phosphodiester bond which links the incorporated NRTI at the end of the DNA, resulting in removal of the NRTI via pyrophosphorolysis. When the pyrophosphate donor is ATP, the NRTI is released as a dinucleoside tetraphosphate product. FIG. 4 illustrates this "primer rescue" in an AZT-terminated DNA (adopted from ClinicCareOptions™).

It is now believed that two distinctive mechanisms are involved in the phenotypic resistance to NRTI (Sluis-Cremer et al, 2000). The first, known as "primer rescue" activity, is described immediately above. Here, the chain-terminating nucleotide is removed from the 3' end of the primer terminus through ATP-dependent or pyrophosphate-dependent pyrophosphorolysis. There is, however, another cluster of resistance phenotypes denoted as "discriminative mutants." These mutants have an RT with enhanced ability to discriminate between NRTIs and native dNTPs. In this case, the mechanism leads to RT which is able to preferentially choose the right substrate (i.e. native dNTP), thereby avoiding chain termination by an NRTI and ensuring the propagation of the viral genome.

Generation of Mutations in HIV

Retroviruses such as HIV have the potential for rapid genetic diversification. While this is an energetically inefficient process, it offers clear adaptive advantages to the organism. The replication machinery used by HIV is particularly error prone, generates a large number of mutations and has the potential to lead to accumulation of mutations when the organism is under selective pressure.

Generally, the vast majority of mutations generated by viral replication result in less viable enzymes. Here, the accumulation of a second and especially a third mutation is less probable because the population pool for the less viable mutant, within which the second mutation must accumulate, will be diluted by the faster multiplying wild type organism.

Yet more viable viral mutants can arise and expand by two possible pathways. The first occurs when there is rapid outgrowth of a highly resistant variant that is already present in the overall viral population. Most frequently this is a single point mutation that confers phenotypic resistance to a selective pressure. In the context of drug escape mutations examples include K103 rapidly induced by the non-nucleoside reverse transcriptase inhibitor nevirapine.

The second pathway occurs when there is continued viral replication in the presence of selective pressure. This allows the progressive accumulation of mutations that can then be expanded. In this case, the probability of mutation accumulation is related to the amount of virus replication that is occurring. That is, at higher viral loads (e.g. >200,000 copies/ml), accumulations of double mutations can occur. Accumulation of triple mutations, however, are rare and can only result as a consequence of a complex therapeutic regimen, typically involving several different drugs, that is challenging for the patient to adhere to. It is therefore extremely difficult for even a diligent patient to ensure that all active ingredients are present in the blood at levels above the necessary inhibitory concentrations over the full 24 hour period of each day "24 hour trough level". Here, temporary removal of any one of the selective pressures of drug treatment due to lapses in the administration/24 hour trough level of one or more drugs allows unbridled viral replication, thereby permitting the generation and establishment of many new mutants. When the selective pressure is once again applied (i.e. resumption of complex drug therapy), the few new mutants that have accumulated another point mutation which confers better drug resistance can expand in a manner similar to that seen for the first pathway (see above).

The discussion above focuses on accumulation of point mutations as opposed to, for example, deletion or addition mutations. Here, however, a scenario similar to that described for a triple mutation is applicable. That is, most deletion/addition mutations initially involve a single nucleotide. This has the effect of completely altering the downstream amino acid sequence of the encoded protein if the change occurs within the coding region and leads to a truncated and/or inactive protein. In order to preserve the reading frame and to alter the final protein by the deletion or addition of one single amino acid, three nucleotides must be deleted/added. Since inactive enzymes reduce the viability of an HIV organism, particularly if the enzyme affected is RT, the deletion/additions will not accumulate per se, but must occur simultaneously. In other words the equivalent of a triple mutation must occur in a single event, which is highly uncommon (see Boyer et al (2004) J Virol 78(18):9987-9997, which is hereby incorporated by reference in its entirety).

As a consequence of this process for triple mutant accumulation/introduction, it was not until relatively recently that HIV virus exhibiting at least three mutations in RT that creates particularly potent resistance to multiple drugs became established. For example, in the United States it was 1992 when the FDA approved the use of combination drug therapy (ddC and AZT). Yet it was not until September of 1995 that clinical trials showed that the combination of AZT with ddC or ddI was more effective than AZT alone. It has only been as a result of the use of combination therapies, where multiple drugs are employed, but in dosage regimes effectively unable to guarantee an adequate 24 hour trough level of the respective drugs, that the particularly problematic strains of multi-resistant HIV virus known in the Western world today have been generated.

Primer Rescue Mutations

The TAM primer rescue mutant originally described comprised various permutations within a group of six drug resistant phenotypes at amino acid positions M41L, D67N, K70R, L210W, T215Y/F and K219Q/E on RT (Larder and Kemp, 1989, Schinazi et al, 2000). Early data pointed to two distinctive mutational pathways for the development of multiple TAM primer rescue mutants, both occurring by unknown factors. The first pathway resulted in an amino acid substitution at codon 210 (210W) and was preferentially associated with mutations at codons 41 (41 L; greater than 98%) and 215 (215Y; greater than 94%) as well as a substitution at codon 67 (67N). The second pathway generated a mutation at codon 219 (219K/E), which was preferentially associated with mutations at codons 67 (67N) and 70 (70R)(Yahi et al, 1999). There were therefore two phenotypic patterns: (1) L210W, M41L, T215Y/F, ±D67N, which conferred high levels of viral resistance to AZT and d4T and (2) K219K/E, D67N, K70R, which conferred moderate levels of viral resistance to AZT and d4T.

Marcelin et al (2004) summarized the prevalence of TAM primer rescue-related mutations in virologic failure pateints. Here, 1098 RT sequences were investigated and gave two genotypic patterns as indicated in FIG. 1 and FIG. 2. While different genetic backgrounds may have been present prior to therapy, the sequence and composition of the antiretroviral therapy undertaken when combined with individual differences in pharmacology resulted in viral resistance not only to AZT and d4T but also to other NRTIs. Depending on the mutational pattern present, drug resistance included abacavir (ABC), didanosine (ddI), tenofovir (TNF), lamivudine (3TC), emtricitabine (FTC) and zalcitabine (ddC). Hence, the emergence of primer rescue-related TAMs often plays an important role in the further development of more pronouncedly resistant HIV genotypic patterns. Therefore, one step in preventing multiple nucleoside resistance is to develop a new NRTI with the goal of avoiding the accumulation of primer rescue related TAMs.

Primer rescue-related TAM mutations can evolve concomitantly with other families of escape mutants that typically emerge from combination antiretroviral therapy (otherwise known as cocktail therapy). Today, the cocktail "combivir" (AZT+3TC) is the most frequently used and recommended first line therapy regimen for treatment of naïve HIV patients. It leads, however, to escape mutants which are resistant to both drugs. For example, Miller et al (1998) reported that 3TC-resistant virus with an M184V mutation was selected just 4-12 weeks after initiation of AZT+3TC combination therapy. In time, additional AZT-associated mutations gradually emerged, giving a characteristic genotypic pattern of M184V, M41L, D67N, K70R, L210W, T215Y/F and K219Q/E which is commonly found in treatment experienced patients today. Additional mutations in RT at positions H208, R211, and L214 (Sturmer et al, 2003) and at position G333 (Kemp et al 1998) are reported to be involved in AZT-3TC double resistance and, in particular, to confer an increase in the ability to resist AZT. Therefore, the genotypic context of primer rescue related TAMs has been expanded to include permutations within M184V, M41L, D67N, K70R, H208Y, L210W, R211K, L214F, T215Y/F, K219Q/E and G333E.

Other types of mutations generally seen in treatment experienced patients are V118I and E44D/A. These mutations are strongly correlated to prior exposure to ddI and d4T. In addition, they are often associated with the presence of specific TAM clusters including M41L plus T215Y/F or D67N plus L210W. The result is increased primer rescue-related TAM resistance to the family of thymidine analogues as well as a distinctive role in the dual resistant to AZT+3TC (Montes et al, 2002, Girouard et al, 2003).

The prevalence of drug escape mutants increases as a function of the number of NRTIs used during the course of therapy and forms a pattern of expanded TAMs or NAMs comprising various permutations within M41L, E44D/A, D67N, K70R, V118 μM184V, H208Y, L210W, R211K, L214F, T215Y/F, K219Q/E and G333E. This cluster is also commonly refractory to AZT- and d4T-containing combination therapies and cross-resistant to the entire class of NRTIs.

Significant resistance to thymidine analogues, notably AZT, d4T and TNF, is also found in escape mutants having an amino acid deletion at position 67(▲67) in the finger region of RT often in association with an amino acid substitution at T69G concomitant with TAM (see Imamichi et al 2000 and 2001). An enhanced RT polymerization activity, which is associated with this particular genotype, is proposed to result in more efficient pyrophosphorolysis-dependent primer excision (described above), leading to the increased resistance Boyer et al, (2004) have also observed that ▲67 concomitant with TAM conferred an increased ability to facilitate primer rescue (excision) viral resistance to AZT and to TNF as compared to TAM alone.

HIV is co-evolving as antiretroviral therapy develops. New mutation phenotypes emerged when double- and triple-nucleoside analogue cocktails were employed in the clinical management of HIV, especially in treatment-naive patients. Complex therapeutic regimens, requiring multiple drugs taken at various times during the day, some with and some without food, are challenging for patients. Failure to comply exactly with these dosing regimes leading to 24 hour trough failures have facilitated the emergence of multiple NRTI resistant HIV viruses, predominantly as a result of virus acquired NAMs or MDRs. For example, a number of groups (e.g. Mas et al, 2000) have observed the emergence of the mutant T69S-XX virus associated with AZT use. This mutant, has a 6-bp insertion in the coding region of its RT between the nucleic acids specifying amino acids 69 and 70. The resulting double amino acid insertion complexes (typically SS, SG or AG insertions) not only led to viral resistance to AZT but also to nearly the entire collection of NRTIs including d4T, 3TC, ddI, ddC and ABC, and TNF. An enhanced pyrophosphorolysis-dependent primer rescue is seen with the T69S+double amino acid insertion, particularly in the presence of TAMs. This phenomenon is typically associated with the "M41L/T215Y" or "M41L/L210W/R211K/L214F/T215Y" resistant phenotypes and plays an important phenotypic role in multiple nucleoside resistance (Meyer et al, 2003).

Another class of MDR has an amino acid substitution at codon Q151M. This mutation is observed at a relatively low frequency in the clinic and often presents together with secondary mutations of A62V, V75I, F77L and F116Y. It confers, however, a significant resistance to nearly the entire class of NRTIs. In addition, it has been associated with TAMs, typically the "M41L, L210W and T215Y/F" or "D67N, K70R and K219K/E" genotypes. It emerges in patients that have experienced heavy treatment with AZT/ddI and AZT/ddC combination regimens.

L74V is most frequently selected by ddI monotherapy (Martin et al, 1993) and displays cross-resistance to ABC and 3TC. Its effect on producing viral escapes is dependent upon the presence of other mutations. Resistance surveys suggest that the frequency of L74V is linked significantly with TAM, typically in an M41L, L210W and T215Y/F background (Marcelin et al, 2004) even though the L74V mutation was thought to cause a diminution effect in viral replication and to resensitize AZT-resistant viruses that contain a number of TAMs (St. Clair et al, 1991). A combination of the L74V and M184V mutations in HIV-1 RT is the most frequent pattern associated with resistance to both ABC and ddI (Harrigan et al, 2000 and Miller et al, 2000).

Although high-level resistance to ABC typically requires multiple mutations comprising K65R, L74V, Y115F and M184V, a single mutation, M184V, often emerges first. This mutation, now recognized as a key mutation in the discriminant mechanism of drug escape resistance, confers a moderate decrease in ABC susceptibility (Tisdale et al, 1997). A CNA3005 study in which a total of 562 patients randomly received AZT and 3TC with either ABC or ddI, showed a slow but steady increase in the proportion of patients carrying a TAM in the AZT and 3TC plus ABC arm. By week 48, up to 56% of the patients had at least one primer rescue-related TAM (1xTAM) over and above the rapidly induced M184V mutation (Melby et al, 2001), illustrating the importance of preventing the emergence of primer rescue-related resistance. Similarly, in vitro passage of AZT-resistant virus bearing the genotypic pattern of 67, 70, 215 and 219 under 3TC selective pressure resulted in the selection of the M184V mutation and conferred cross-resistance to ABC (Tisdale et al, 1997). This again highlights the concept that treating the pre-existing of primer rescue-related TAM and preventing the accumulation of primer rescue-related mutants is a pivotal step in avoiding development of multiple nucleoside resistance.

It has become increasingly clear that the K65R mutation quickly appears in a very high proportion of patients who are receiving TNF or ABC. Valer et al (2004) reported that K65R increased in prevalence in their Madrid hospital from <1% between 1997-2000 to 7% in 2003 and 12% in the first 4 months of 2004. The effect of the K65R mutant is exacerbated in the presence of other mutations associated with decreased susceptibility to ABC, 3TC, ddI and ddC (Parikh et al, 2003). Yet the simultaneous appearance of K65R of primer rescue-related TAM genotypes, although rarely occurring, leads to a more profound effect on the primer rescue (excision) of TNF than of AZT (Naeger et al, 2001). TNF was reported to be active against HIV-1 with up to 3xTAMs unless the TAM cluster included an M41L or L210W mutation. Currently it is unclear why TAMs could reverse some of the effects of K65R, which is otherwise thought to impede primer excision mutants with respect to susceptibility to TNF and ABC.

Finally, the T69D mutation was initially identified for its role in causing ddC resistance. It has also been reported to be associated with a decreased response to ddI when it occurs in combination with the T215Y mutation and other of primer rescue-related TAM genotypes.

For many years the WHO and DHHS (US Department of Health and Human Health Service) have recommended first-line antiretroviral therapy on treatment naïve patients consisting of administering d4T or AZT in combination with 3TC plus nevirapine or efavirenz (Guidelines for the Use of Antiviral Retroviral Agents in HIV-1-Infected Adults and Adolescents, Jul. 14, 2003 and Mar. 23, 2004). A substantial number of HIV-infected patients have, however, experienced treatment failure while on their initial highly active antiretroviral therapy (HAART) regimens, suggesting that these patients are already infected with drug escape viruses. Primer rescue-related TAM resistance mutants continue to play a pivotal role in the development of drug resistance. Thus the development of drugs or therapeutic methods that counteract the effect of primer rescue-related TAM resistance mutants could potentiate or prolong the use of existing NRTIs for treating treatment-naïve patients and could also be used to treat the primer rescue-related resistance mutant-carrying HIV infected population in a salvage therapy.

Drug Strategies for Preventing/Inhibiting Primer-Rescue Mutants

Primer rescue and discriminative mutations often appear together in the same mutant genotype, largely due to current therapeutic strategy. A M184V mutation is representative of the family of discriminative mutants. If, however, it occurs in conjunction with primer rescue-related mutants such as M41L, D67N, K70R, L210W, T215Y/F, and K219Q/E, it plays a role in the dual resistance to AZT and 3TC (Miller et al., 1998).

These primer rescue and discriminative resistance phenotypes seem to correlate with different clusters of mutations in RT. For example, AZT-associated mutations comprising various permutations within M41L, E44D/A, D67N, K70R, V118I, M184V, H208Y, L210W, R211K, L214F, T215Y/F, K219Q/E and G333E, an MDR T69S mutation with 6-bp insertions and a ▲67 typically exhibit primer rescue mutant activities. On the other hand, mutations at positions 65, 74, 89, 151, and 184 lead to the ability to discriminate between NRTIs and the respective dNTP counterparts or they may be involved in the repositioning of the primer-template complex.

In the recent article "Designing anti-AIDS drugs targeting the major mechanism of HIV-1 RT resistance to nucleoside analog drugs" (IJBCB 36 (2004) 1706-1715, which is hereby incorporated by reference in its entirety), Sarafianos et al conclude that the primer rescue (excision) mechanism could only occur before RT translocation at the N-site and further conclude that it has become the dominant mechanism of NRTI resistance. In the chapter entitled "Strategies for Inhibition of the Excision Reaction" (see page 1711), they propose three approaches to defeat such a resistance mechanism:

1. use of new antivirals that interfere with the productive binding of ATP (at the P site), presumably by binding at or near the ATP-binding site, thereby blocking the excision reaction without affecting the forward reaction of DNA synthesis.
2. use of compounds that can block DNA synthesis but are somehow resistant to excision, such as borano- or thio-substituted alpha phosphate variants of the current NRTIs. Similarly, variants of the current NRTIs can be engineered to reposition the extended/terminated template/primer in a non-excisable mode, as suggested by the poor excision capacity of the M184I/V mutants induced by 3TC.
3. use of dinucleotide tetraphosphate based inhibitors to provide bi-dentate binding at both N- and P-sites.

Each of these three proposed approaches to preventing primer rescue mechanisms of NRTI resistance is open to criticism for various theoretical shortcomings. For example, in the first approach ATP binding is not required for normal RT functions. Thus, countermeasures based on inhibiting ATP or pyrophosphate binding by competition or blockage will not prevent resistance development because the fitness of the underlying virus will not be compromised by such agents. In other words, resistance mutations will arise at no evolutionary cost. The abundant amount of ATP present in normal lymphocytes also challenges the rationale behind this approach.

In the second proposed approach, it seems likely that borano- or thio-substituted alpha phosphate analogues would select for the discriminative resistant mutants, as has been seen with 3TC and FTC, and produce HIV resistance mutants.

The third proposed approach is limited by the need for pharmacokinetic uptake into the target cell of the large and highly charged tetraphosphate dinucleotide species. This will be a severe pharmaceutical and drug delivery challenge.

It is noteworthy that each of Serafaniano's approaches, including approach 1 which is not antiviral in itself, but presupposes co-administration of a conventional NRTI, is based on variants of the current generation of NRTIs. That is, compounds that lack a 3-hydroxyl function and therefore act as obligate chain terminators.

In contrast to the "classic" NRTIs discussed above (i.e. those lacking a 3'-hydroxy function), Ohrui et al (J Med Chem (2000) 43, 4516-4525, which is hereby incorporated by reference in its entirety) describe 4'-C-ethynyl HIV inhibitors:

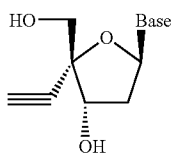

Formula I

These compounds retain the 3'-hydroxy function but nevertheless exhibit activity against HIV-1, including a typical discriminative MDR strain bearing the A62V, V75L, F77L, F116Y and Q151 M mutations. The mechanism of action was postulated to be through affinity to the nucleoside phosphorylating kinase. It was, however, also observed that these compounds may be functioning as DNA chain terminators due to their neopentyl alcohol character and the severe steric hindrance of the vicinal cis 4' substituent, which resulted in a sharply diminished reactivity of the 3'-hydroxy.

Kodama et al (Antimicrob Agents Chemother (2001) 1539-1546, which is hereby incorporated by reference in its entirety) describe a very similar set of compounds bearing a 4'-C-ethynyl group adjacent to the retained 3'-hydroxy function that were assayed in cell culture with additional HIV resistant strains. Since Kodama et al did not prepare the triphosphates of their compounds, they were unable to elucidate the mechanism of action but infer from various circumstantial observations that the compounds are indeed acting as NRTIs. Kodama et al later reported (abstract 388-T, 2003 $9^{th}$ Conference on Retroviruses and Opportunistic Infections, which is hereby incorporated by reference in its entirety) that under the selective pressure of their 4-C-ethynyl nucleoside in vitro, breakthrough resistant HIV bearing T165I and M184V mutations located in the RT catalytic site were found. This mutant phenotype is manifestly a discriminative type of mutation and is heavily cross resistant to 3TC. Steric conflict blocking 4-C-ethynyl nucleoside incorporation was thus implicated. This has been established with the 3TC inhibitory mechanism and therefore almost certainly represents the discriminative resistant mechanism. It therefore seems unlikely that the Kodama compounds will provide guidance in addressing the mutants facilitating primer rescue (ATP or pyrophosphate mediated excision).

Chen et al (Biochemistry (1993) 32:6000-6002, which is hereby incorporated by reference in its entirety) conducted extensive mechanistic investigations on a structurally related series of compounds bearing an azido group at 4':

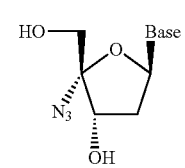

Formula II

Chen demonstrated that RT efficiently incorporates two consecutive 4'-azidothymidine monophosphate nucleotides, which terminates chain elongation. In addition, RT was also able to incorporate a first 4'-azidothymidine monophosphate, followed by a native dNTP and a then a second 4'-azidothymidine nucleotide, which also led to chain termination. Note that both of these mechanisms resulted in a 4'-azidothymidine monophosphate residing at the terminated DNA primer terminus, which is an inhibitory mechanism very reminiscent of the current NRTIs. It was also apparent that the cellular (ie non-viral) polymerases a and B were each able to incorporate a single 4'-azido nucleotide, but not a second, into the nascent chain of the host DNA. These cellular polymerases then allowed the host DNA chain to elongate with further native dNTPs and so permanently incorporated the NRTI nucleotide into host DNA genes. These compounds have not been pursued in humans because misincorporation of non-native nucleotides by cellular enzymes has clear implications in carcinogenesis. Similarly, the pharmaceutical development of the Kodama corresponding 4'-C-ethynyl compounds was stopped, allegedly due to severe toxicity in higher organisms.

EP 341 911 describes an extensive family of 3'-C-hydroxymethyl nucleosides of the formula

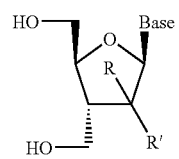

Formula III and proposes their use predominantly against herpesviruses such as CMV, but also against retroviruses. WO92/06201 also discloses a similar set of compounds and indications.

U.S. Pat. No. 5,612,319 (which is hereby incorporated by reference in its entirety) discloses the retroviral activity of 2'-3' dideoxy-3'-C-hydroxymethylcytidine against wild type HIV-1$_{IIIB}$ and the simian equivalent, SIV-1, in an acute cynomolgus monkey model of HIV infection. This publication proposes the use of the compound as a post-exposure prophylaxis agent, especially against needle-stick injuries. Post exposure prophylaxis implies that the active ingredient is immediately administered to people such as medical personnel, who have unwittingly jabbed themselves with a potentially HIV-infected syringe. In order to ensure rapid treatment of an understandably shocked health care professional, a self administered spring-loaded syringe, such as are used for antidotes to chemical and biological warfare, is a preferred administration route.

The intention of post-exposure prophylaxis is to prevent the infection from establishing itself rather than treating an on-going infection. As such, it was intended that treatment was to be carried out for a short time period such as 24-48 hours, using extremely high doses of the compound. This publication states that because of the discrete time period of administration, transient toxicity is acceptable because one is trying to prevent an incurable disease. The post-exposure prophylactic method described in U.S. Pat. No. 5,612,319 has never been tried in humans—indeed to our knowledge 2'-3' dideoxy-3'-C-hydroxymethylcytidine has not been administered to humans at all.

In 1994 when the application granting as U.S. Pat. No. 5,612,319 was filed, multi-resistant HIV as it is known today had not arisen in any cogent form. Today's multi-resistant HIV has primer rescue mutations induced by and accumulated from many years of selective pressure from NRTI therapy. In other words, the HIV and especially the RT existent at the time these patents were granted was structurally and mechanistically very different from today's viruses.

BRIEF DESCRIPTION OF THE INVENTION

The current invention provides a method for the treatment of an HIV patient where the RT of the HIV bears at least one primer rescue mutation that allows an obligate chain terminating nucleoside- or nucleotide phosphate to be excised from the nascent DNA strand by ATP- or pyrophosphate-mediated excision. The method comprises administering to the patient an effective amount of 2',3'-dideoxy-3'-hydroxymethylcytidine or a salt thereof.

Another embodiment of the invention provides a method for inhibiting the emergence or propagation of HIV primer rescue mutants that are able to remove a chain-terminating NRTI nucleotide incorporated into an HIV primer/template complex where the removal is effected by an ATP-dependent or pyrophosphate dependent excision mechanism. The method comprises the simultaneous or sequential administration to an individual infected with HIV an effective amount of 2',3'-dideoxy-3'-hydroxymethylcytidine and at least one chain terminator NRTI which induces primer rescue mutants.

According to the present invention there is also provided the use of 2',3'-dideoxy-3'-hydroxymethylcytidine or a salt thereof in the manufacture of a medicament for the treatment of HIV infection wherein the reverse transcriptase of the HIV bears at least one mutation that allows an obligate chain terminating nucleoside- or nucleotide phosphate to be excised from the nascent DNA strand by ATP- or pyrophosphate-mediated excision.

There is also provided 2',3'-dideoxy-3'-hydroxymethylcytidine or a salt thereof for use in the treatment of HIV infection wherein the reverse transcriptase of the HIV bears at least one mutation that allows an obligate chain terminating nucleoside- or nucleotide phosphate to be excised from the nascent DNA strand by ATP- or pyrophosphate-mediated excision.

Further, there is provided the use of 2',3'-dideoxy-3'-C-hydroxymethylcytidine or a salt thereof together with at least one chain terminator NRTI as active ingredients in the manufacture of a medicament for simultaneous or sequential administration of said active ingredients for the inhibition of the emergence or propagation of HIV mutants in an individual infected with HIV, wherein said mutants are able to remove a chain-terminating NRTI nucleotide incorporated into an HIV primer/template complex, the removal being facilitated by an ATP-dependent or pyrophosphate dependent excision mechanism.

There is also provided 2',3'-dideoxy-3'-C-hydroxymethylcytidine or a salt thereof together with at least one chain terminator NRTI as active ingredients for use for simultaneous or sequential administration of said active ingredients for the inhibition of the emergence or propagation of HIV mutants in an individual infected with HIV, wherein said mutants are able to remove a chain-terminating NRTI nucleotide incorporated into an HIV primer/template complex, the removal being facilitated by an ATP-dependent or pyrophosphate dependent excision mechanism.

In the uses and methods of the invention the 2',3'-dideoxy-3'-C-hydroxymethylcytidine may if desired be employed in the form of a prodrug thereof releasing 2',3'-dideoxy-3'-C-hydroxymethylcytidine or its 5'-monophosphate in vivo.

Although not wishing to be bound by this proposed mechanism it is believed that 2',3'-dideoxy-3'-C-hydroxymethylcytidine is phosphorylated to the corresponding 5'-triphosphate by cellular enzymes. The heavily mutated RT of multiresistant HIV, in particular primer rescue-related mutant RT, incorporates this triphosphate as the 5'-(2',3'-dideoxy-3'-C-hydroxymethylcytidine) monophosphate into the nascent DNA chain.

Conventional NRTIs act as obligate chain terminators, terminating DNA synthesis at the N-site, and are thus susceptible to the above described ATP- or pyrophosphate mediated primer rescue (excision) mechanism unique to mutiresistant HIV. In contrast, the evidence presented herein suggests that 5'-(2',3'-dideoxy-3'-C-hydroxymethylcytidine) monophosphate does not act as an obligate chain terminator, but rather allows an additional residue to be covalently attached to the 3' hydroxymethyl function of the 5'-(2',3'-dideoxy-3'-C-hydroxymethylcytidine) monophosphate. This then promotes the RT to undergo the necessary transformational change to translocate itself into the P-site for the next round of polymerization. Preliminary evidence based on the sequence of the template presented below suggests that this attached terminal residue is a native nucleotide rather than a further 5'-(2',3'-dideoxy-3'-C-hydroxymethyl cytosine) monophosphate.

Importantly, the evidence obtained using the methods of the invention and presented below suggests that the last incorporated, non-2'3'-dideoxy-3'-C-hydroxymethylcytidine nucleotide is not amenable to the further addition of nucleotides by the mutated reverse transcriptase. That is, chain termination appears to occur one base beyond the NRTI of the invention rather than at the NRTI. Furthermore, following the incorporation of the compound of the invention, the RT appears to successfully translocate to the P-site in order to accept the next incoming nucleotide. This evidence suggests that the compound of the invention, in conjunction with a primer rescue-related mutated RT, achieves a form of chain termination which is not amenable to ATP- or pyrophosphate induced excision. As a consequence, the claimed method allows effective treatment of HIV infections that are non-responsive to current drug regimes.

The inhibitory mechanism discussed immediately above is thus fundamentally different from the chain termination mechanism of the 4'-substituted nucleosides of Chen et al (see above), which allows several nucleotides to be incorporated after the incorporated 4-substituted compound. Firstly, the Chen mechanism dramatically enhances the risk of "readthrough." That is, the DNA polymerase continues to follow the coding strand and continues to add the coded residues to the normal stop codon, thereby misincorporating the abnormal nucleoside within the DNA strand. Antiviral efficacy can be lost, however, when a viral DNA strand is constructed by the viral polymerase (i.e. RT) since the readthrough construct may still be viable, notwithstanding the misincorporated 4'-substituted nucleoside. More importantly, if the 4'-substituted nucleoside is readthrough by a cellular (i.e. host) polymerase, as Chen describes, the resulting construct thereafter represents a teratogen and dramatically increases the risk of cellular damage and cancer.

The Chen compounds additionally require the addition of a second 4'-substituted nucleotide, either immediately adjacent to the first mis-incorporated 4'-substituted nucleotide (i.e. X-X) or interspersed by one native nucleotide (i.e. X—N—X). In practice this means that the nucleotide at the last position of the primer terminus is the non-native (i.e. drug) nucleotide. This is an analogous situation to the case of classic NRTIs (i.e. those lacking a 3-hydroxy group) chain termination. Here, the NRTI nucleotide also resides at the last position of the primer terminus where, as discussed above, it is susceptible to ATP or pyrophosphate mediated excision.

Multiple units of the Chen 4'-substituted nucleotide are needed in order for it to work as an efficient RT inhibitor. As a consequence, the drug's effectiveness depends on the sequence of the reading strand. For example, if the Chen compound is a thymidine analogue it will have the best affinity if the reading strand has an AA or A-N-A sequence. Here, the drug would be efficient and effective in terminating DNA synthesis. But if the reading strand's sequence does not contain abundant recitals of the AA or A-N-A sequence, the Chen drug will be less able to terminate DNA synthesis, at a given concentration. Since an AA doublet or an A-N-A triplet is far less common in the genome than a singlet A, the Chen drug will be far less efficient than other NRTIs that do not have a multiple unit requirement.

The multiresistant HIV treated or prevented according to the invention will typically have an RT bearing a genetic pattern comprising at least one of (a) M41, ±D67, L210 and T215;

(b) D67, K70 and K219;

(c) T69S-XX or (d) ▲67 where XX represents an addition to the RT sequence of any two natural amino acids and ▲67 represent the amino acid deletion at codon 67.

Although the above 4 genetic patterns are believed to represent the essential basis of the excision drug escape phenotype, it will be apparent that the mutants treated or prevented by the use of the invention will typically comprise additional mutations in the RT gene and elsewhere, often at least three mutations in the RT gene.

Generally, but not exclusively, the cluster M41, ±D67, L210 and T215 will often comprise M41L, ±D67N, L210W and T215Y or T215F.

Optionally, the clusters immediately above may further comprises at least one further mutation at position E44, K70, V118, H208, R211K, L214, K219 or G333.

The clusters immediately above may further comprise at least one additional mutation at position ▲67, T69, E203, L210, D218, H221, D223 or L228.

Generally, but not exclusively, the cluster D67, K70 and K219 comprises D67N, K70R and K219Q or K219E.

Optionally, the cluster D67, K70 and K219 may further comprise at least one additional mutation at position M41, E44, V118, H208, L210, R211K, L214, T215, or G333.

In addition, the cluster D67, K70 and K219 optionally further comprises at least one additional mutation at position ▲67, T69, E203, L210, D218, H221, D223 or L228.

Generally, but not exclusively, the cluster T69S-XX may further comprise at least one additional mutation at position M41, E44, D67, K70, V118, H208, L210, R211K, L214, T215, K219 or G333.

Optionally, the cluster T69S-XX may further comprise at least one additional mutation at position ▲67, T69, E203, L210, D218, H221, D223 or L228.

Generally, but not exclusively, the cluster ▲67 may further comprise at least one additional mutation at position M41, E44, D67, K70, V118, H208, L210, R211K, L214, T215, K219 or G333.

Optionally, the cluster ▲67 may further comprise at least one additional mutation at position T69, T69S+XX, E203, L210, D218, H221, D223 or L228.

Optionally, the reverse transcriptase may further bear at least one discriminative mutation at position K65, L74, M184 or Q151, especially K65R, L74V or M184V or Q151M.

Typically, the cluster of discriminative mutants may be linked with at least one additional mutation at position A62, V75, F77, Y115 or F116.

The HIV strains treated by the invention are multiresistant HIV strains whose RT has mutations that encourage ATP- or pyrophosphate-mediated primer rescue (excision) of chain terminating NRTI nucleotides and which has arisen within the patient as a result of previous HIV-treatment with at least one antiviral selected from zudovudine (AZT, ZDV), stavudine (d4T), zalcitabine (ddC), didanosine (ddI), abacavir, (ABC), lamivudine (3TC), emtricitabine (FTC), adefovir (ADV), entacavir (BMS 200475) alovudine (FLT), tenofovir disoproxil fumarate (TNF), amdoxavir (DAPD), D-d4FC (DPC-817), -dOTC(SPD754), SPD-756, racivir, D-FDOC or GS7340. Alternatively, the HIV strains are those found in patients who have received such a resistant or multiresistant HIV strain directly or indirectly from another individual who had themselves induced a resistant or multiresistant HIV strain by sustained treatment with at least one antiviral from the above list of NRTI antivirals. Frequently the mulitresistant HIV strains contain at least three mutations in the viral RT as compared to wildtype.

It will thus be apparent that the methods and composition of the invention may be used as an add-on to current antiretroviral therapies, such as HAART, or in some cases as a rescue or salvage therapy. This will typically be the case where the multiresistant HIV has been induced in the actual patient by that patient's earlier antiretroviral drug treatment history. Alternatively, the methods and compositions of the invention will constitute a first line therapy, typically in patients whose primary HIV infection occurred with an already-mutated multiresistant strain. The following antiviral drugs often induce such multiresistant HIV strains having RT primer rescue mutations which encourage ATP- or pyrophosphate-mediated excision of chain terminating NRTI nucleotides:

zudovudine, lamivudine or the combined dosage forms Combivir or Trizivir; lamivudine, abacavir or the combined dosage form Epzicom;

tenofovir, emtricitabine or the combined dosage form Truvada.

While these drugs frequently induce such multiresistant HIV strains, this drug list is not exclusive.

It is therefore apparent that the 2',3'-dideoxy-3'-C-hydroxymethylcytidine is administered in order to prevent the emergence of one or more multiresistant HIV strains having RT primer rescue mutations that encourage ATP- or pyrophosphate-mediated excision of chain terminating NRTI nucleotides. This prevention occurs even when NTRI drugs which induce such mutations are administered concomitantly.

A third aspect of the invention provides a pharmaceutical composition in unit dosage form or co-dosage form comprising 2',3'-dideoxy-3'-C-hydroxymethylcytidine and at least one chain terminator NRTI, where upon sustained dosing with the NRTI induces, HIV RT primer rescue mutations which encourage ATP-dependent or pyrophosphate-dependent excision of incorporated NRTI monophosphate from the 3'-terminus of the primer/template complex and allows resumption of DNA synthesis.

Preferred embodiments of the pharmaceutical composition of the invention and the method of the invention include those where the NRTI is selected from zudovudine (AZT, ZDV), stavudine (d4T), zalcitabine (ddC), didanosine (ddI), abacavir, (ABC), lamivudine (3TC), emtricitabine (FTC), adefovir (ADV), entacavir (BMS 200475), alovudine (FLT), tenofovir disoproxil fumarate (TNF), amdoxavir (DAPD), D-d4FC (DPC-817), -dOTC (SPD754), SPD-756, racivir, D-FDOC or GS7340 and combinations thereof.

Particularly preferred embodiments include those where the NRTI is selected from: zidovudine, stavudine, didanosine, lamivudine, abacavir, tenofovir, emtricitabine or combinations thereof.

In contrast to the methods disclosed in U.S. Pat. No. 5,612,319, the 2',3'-dideoxy-3'-C-hydroxymethylcytidine of the invention is administered to the patient at a relatively low dose and with the expectation of a sustained and protracted antiretroviral treatment. This defined dosage treatment regimen ensures defined drug levels and avoids toxicity, unlike a post-exposure prophylaxis treatment where transient toxicity is acceptable. U.S. Pat. No. 5,612,319 suggests doses of 2',3'-dideoxy-3'-C-hydroxymethylcytidine of about 10-25 mg/kg/day for human post-exposure prophylaxis treatment and used 30 mg/kg/day in the monkey experiments.

In the current invention, however, the 2',3'-dideoxy-3'-C-hydroxymethylcytidine is administered at less than 1 mg/kg/day, preferably in the range of 0.05-0.5 mg/kg/day and most preferably at less than 0.1 mg/kg/day. The appropriate dosage will depend upon the indications and the patient, and is readily determined by conventional animal drug metabolism and pharmacokinetics (DMPK) or clinical trials and in silico prediction software.

The unit dosage or co-dosage pharmaceutical compositions of the invention have corresponding amounts of 2',3'-dideoxy-3'-C-hydroxymethylcytidine, typically scaled for a 60 kg or 75 kg adult, and are optionally divided once, twice or three times for a QD, BID or TID dosage regime. Dosages are scaled upward if a prodrug is employed in order to account for the extra mass of the prodrug and scaled downward in view of the enhanced bioavailability. If the therapeutic dose is in the range of 0.05-0.5 mg/kg/day, then a clinical QD dose per person per day would be 3 mg-30 mg for a 60 kg adult or 3.75-37.5 mg for a 75 kg adult. Dosage and regiment restrictions of the additional conventional NRTI in the combined dosage unit pharmaceutical composition aspect of the invention may necessitate QD, BID or TID dosing.

Co-dosage forms include single packages containing blister packs of 2',3'-dideoxy-3'-C-hydroxymethylcytidine or its prodrug and a further NRTI as defined above. The blister pack may include blisters for both components on the one blister sheet (typically with indicia facilitating the correct administration of the appropriate number of tablets/capsules of each—for example 2 tablets of one drug and 1 tablet of the other. Alternatively the co-dosage form is a package with a plurality of blister sheets enclosed, wherein each of the drugs has its won blister sheet.

The newly appreciated principle that 2'3'-dideoxy-3-C-hydroxymethylcytidine in the context of HIV RT which is mutated so as to allow chain terminator excision by a pyrophosphoyltically catalysed route, is operating by a different mechanism of action from chain terminating nucleosides may be put into effect by administration of the parent compound 2'3'-dideoxy-3-C-hydroxymethylcytidine, or by the administration of prodrugs which release 2'3'-dideoxy-3-C-hydroxymethylcytidine in vivo.

One group of prodrugs of 2'3'-dideoxy-3-C-hydroxymethylcytidine employs base modification, as shown in Mauldon et al Biorg Med Chem 6 (1998) 577-585. Typical base modified prodrugs have the formula:

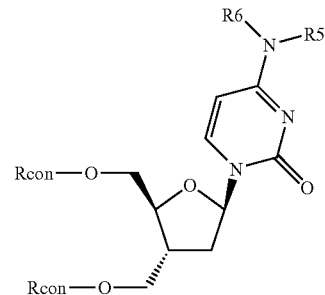

where Rcon is independently H or a conventional pharmaceutically acceptable ester;
$R^5$ is —C(=O)$R^7$, or an amide-bound L-amino acid residue;
$R^6$ is H;
or $R^5$ and $R^6$ together define the imine =$CR^8R^{8'}$;
$R^7$ is $C_1$-$C_6$ alkyl, $C_0$-$C_3$alkylcycyl;
$R^8$ and $R^{8'}$ are independently H, $C_1$-$C_6$ alkyl, $C_0$-$C_3$alkylcycyl;
or $R^8$ is H and $R^{8'}$ is —$NR^9R^{9'}$;
$R^9$ and $R^{9'}$ are independently H, $C_1$-$C_6$ alkyl, $C_0$-$C_3$alkylcycyl;
or $R^9$ and $R^{9'}$ together with the N atom to which they are attached define a saturated 5 or 6 membered ring;
n is 1, 2 or 3;

Conventional pharmaceutically acceptable esters include alkyl esters such as acetyl, propionyl, butyryl, pivaloyl, palmityl, stearyl and the like and aryl esters such as benzoyl. Other conventional pharmaceutically acceptable esters include amino acid esters such as L-valyl, L-isoleucine or L-phenylalanine.

Examples of base modified prodrugs of 2',3'-dideoxy-3'-C-hydroxymethyl in Mauldon include the imines:
—N=CHNR,
where NR is N($CH_3$)2, N(iPr)$_2$, N(Pr)$_2$, N($CH_2$)$_4$, N($CH_2$)$_5$, N($CH_2$)$_6$, N($CH_2CH_2$)$_2$O Further Mauldon base modified prodrugs include the amides of the cytosine nitrogen

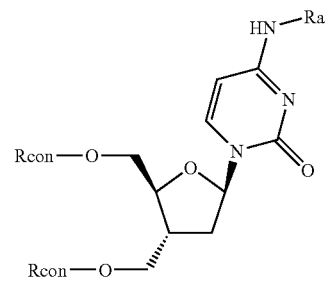

where Rcon is H or a conventional pharmaceutically acceptable ester,
Ra is NH(Boc-LValyl), NH-Boc L-Phe, L-valyl, L-Phe;

or Ra is C(=O)CH$_3$, COPh, COC(CH$_3$)$_3$ and the like

Base modified prodrugs such as Mauldin may have the advantage of decreasing susceptibility to cellular and physiological cytosine deaminases, but in view of the many transglycolsylation reactions occurring in human cells, care must be taken to ensure that the modified base is not transglycoslated onto a native riboside and incorporated into human DNA with cancerogenic or tautogenic consequences.

A preferred group of prodrugs of 2'3'-dideoxy-3'-C-hydroxymethylcytidine useful for the invention are 3' and/or 5' ester prodrugs of the formula:

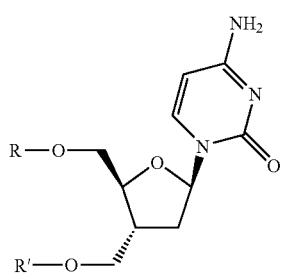

V where one of R and R' is a prodrug moiety with the partial structure:

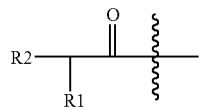

where R$^1$ is H or C$_1$-C$_{18}$ straight or branched alkyl;

R$^2$ is H or NHR$^3$

R$^3$ is H or an L-valyl or L-isoleucyl ester;

and the other one of R and R' is H or an identical prodrug moiety;

or a pharmaceutically acceptable salt thereof.

Many of these ester prodrugs or 2,'3'-dideoxy-3-'C' hydroxymethylctyosine are novel compounds and form an additional aspect of the invention.

One embodiment of the ester prodrugs of the invention includes compounds of the formula V wherein R$^1$ is C$_1$-C$_{18}$ straight or branched chain alkyl and R$^2$ is H. Representative alkyl moieties include those defining the esters octanoyl (C8, including the ketone C), decanoyl (C$_{10}$), lauryl (C$_{12}$), myristoyl (C$_{14}$), palmitoyl (C$_{16}$), stearoyl (C$_{18}$) or eicosanoyl (C$_{20}$). Preferred alkyl moieties include methyl (ie acetyl) ethyl, n-propyl, iso-propyl, n-butyl, iso-butyl, sec-butyl, t-butyl (ie pivolaloyl), n-pentyl, 1-methylbutyl, 2,2-dimethylbutyl, 2-methylpentyl, 2,2-dim ethylpropyl, n-hexyl and the like. The prodrug may bear an ester at R (ie a 5'-0 ester) or R' (ie a 3'-O-ester) or both (a bis 3',5'-O-ester). For ease of synthesis and analysis it is preferable, but obligatory, that the esters on 3' and 5' are identical prodrug moieties.

A further embodiment of the ester prodrugs of the invention include those wherein R$^1$ is lower alkyl, especially methyl and R$^2$ is NHRb, where Rb is the residue of an L-aliphatic amino acid selected from alanine, valine, leucine, t-leucine, isoleucine and norleucine, especially wherein R$^2$ is NH-L-valyl or NH-L-isoleucyl. In this embodiment R$^1$ has the stereochemistry corresponding to L-lactic acid. The prodrug may bear this ester prodrug moiety at R (ie a 5'-0 ester) or R' (ie a 3'-O-ester) or both (a bis 3',5'-O-ester). For ease of synthesis and analysis it is preferable, but obligatory, that the esters on 3' and 5' are identical prodrug moieties.

Further ester prodrugs for use in the invention include those wherein R$^1$ is branched chain C$_3$-C$_4$ alkyl and R$^2$ is NH$_2$. The R$^1$ side chain preferably has the stereochemistry of an L-amino acid such as L-valine, L-leucine, L-isoleucine, or L-t-leucine. The prodrug may bear an ester at R (ie a 5'-0 ester) or R' (ie a 3'-O-ester) or both (a bis 3',5'-O-ester). For ease of synthesis and analysis it is preferable, but obligatory, that the esters on 3' and 5' are identical prodrug moieties.

Preferred prodrugs include

5'-O-L-valyl-2',3'-dideoxy-3'-C-hydroxymethylcytidine;
5'-O-L-isoleucyl-2',3'-dideoxy-3'-C-hydroxymethylcytidine;
5'-O-acetyl-2'-3'-dideoxy-3-C-hydroxymethylcytidine;
5'-O-propionyl-2'-3'-dideoxy-3-C-hydroxymethylcytidine;
5'-O-butyryl-2'-3'-dideoxy-3-C-hydroxymethylcytidine;
5'-O-pivaloyl-2'-3'-dideoxy-3-C-hydroxymethylcytidine;
2'-3'-dideoxy-3-C-(acetyl-oxymethyl)cytosine;
2'-3'-dideoxy-3-C-(propionyl-oxymethyl)cytosine;
2'-3'-dideoxy-3-C-(butyryl-oxymethyl)cytosine;
2'-3'-dideoxy-3-C-(pivaloyl-oxymethyl)cytosine;
2'-3'-dideoxy-3-C-(L-valyl-oxymethyl)cytosine;
2'-3'-dideoxy-3-C-(L-isoleucyl-oxymethyl)cytosine;
5'-O-L-valyl-2',3'-dideoxy-3'-C-L-valyloxymethylcytosine;
5'-O-L-isoleucyl-2',3'-dideoxy-3'-C-L-isoleucyloxymethylcytosine;
5'-O-acetyl-2'-3'-dideoxy-3-C-acetyloxymethylcytosine;
5'-O-propionyl-2'-3'-dideoxy-3-C-propionyoxymethylcytosine;
5'-O-butyryl-2'-3'-dideoxy-3-C-butyryloxymethylcytosine;
5'-O-pivaloyl-2'-3'-dideoxy-3-C-pivaloyloxymethylcytosine;
and pharmaceutically acceptable salts thereof.

Particularly preferred prodrugs include

5'-O-[2-S-(L-valyloxy)-propionyl]-2'-3'-dideoxy-3-C-hydroxymethylcytidine,
2',3'-dideoxy-3'-C-[2-S-(L-valyloxy)-propionyl]-oxymethylcytosine;
5'-O-pentanoyl-2'-3'-dideoxy-3-C-hydroxymethylcytidine;,
2',3'-dideoxy-3'-C-pentanoyl-oxymethylcytosine; or
5'-O-pentanoyl-2'-3'-dideoxy-3-C-pentanoyl-oxymethylcytosine;
or a pharmaceutically acceptable salt thereof, Although not wishing to be bound by theory, it is believed that 2'3'-dideoxy-3-C-hydroxymethylcytidine, like other nucleoside analogues, is phosphorylated intracellularly by cellular kinases to the 5'-monophosphate, which in turn is further phosphorylated to the diphosphate and triphosphate. Di and tri-phosphorylating kinases tend to be more active than the initial monophosphorylating kinase, especially in some cell types. In other words monophosphorylation can be theoretically be a rate limiting step. Accordingly in some circumstances it may be convenient to administer the parent compound in a ready-monophosphorylated form, in order to ensure rapid onward phosphorylation to the triphosphate. However it is not straightforward to get a highly polar drug such as a nucleoside monophosphate through the cell membrane. There are, however, prodrug handles which are believed to allow intracellular penetration of the prodrug which is hydrolysed in situ to the monophosphate. One such approach is exemplified by the phase II zidovudine prodrug fozivudine tidoxil which employs a lipid thioether conjugate to the phosphate ester of zidovudine. See for example Girard in JAIDS 23 227-235 and U.S. Pat. No. 5,756,711 U.S. Pat.

No. 5 563 257 and EP 545 966. The analogous construction applied to the 5'-monophsophate of 2'3'-dideoxy-3'-C-hydroxymethylcytsine is:

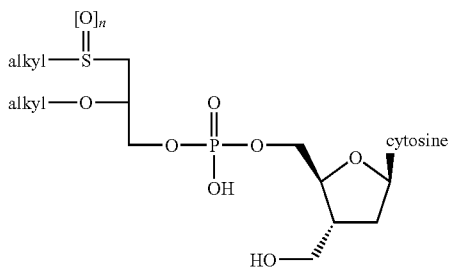

where alkyl is typically $C_8$-$C_{15}$ and n is 0 (mercapto) 1 (sulphinyl) or 2 (sulphonyl). Favoured values include dodecylmercapto in conjunction with a decyl ether.

In the context of the invention a prodrug of 2'3'-dideoxy-3-C-hydroxymethylcytidine also includes prodrugs of the 5'-monophosphate releasing 2'3'-dideoxy-3-C-hydroxymethylcytidine-5-O-phosphate intracellularly.

The current invention includes pharmaceutically acceptable salts such as salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate. Also included are the salts of organic sulphonic acids such as methanesulphonate, ethanesulphonate, 2-hydroxyethane sulphonate, camphorsulphonate, 2-napthalenesulphonate, benzenesulphonate, p-chloro-benzenesulphonate and p-toluenesulphonate. The acceptable salts also include those from inorganic acids such as hydrochloride, hydrobromide, hydroiodide, sulphate, bisulphate, hemisulphate, thiocyanate, persulphate, phosphoric and sulphonic acids.

The current invention extends to active agents that are hydrates, solvates, complexes and other physical forms releasing 2',3'-dideoxy-3'-C-hydroxmethylcytosine in vivo.

While it is possible for the active agent to be administered alone, it is preferable to present it as part of a pharmaceutical formulation. Such a formulation will comprise the 2',3'-dideoxy-3'-C-hydroxmethylcytosine active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration. Preferably the formulation is an orally administered formulation. The formulations may conveniently be presented in unit dosage form, e.g. tablets and sustained release capsules, and may be prepared by any methods well known in the art of pharmacy.

Such well known methods include the step of bringing the 2',3'-dideoxy-3'-C-hydroxmethylcytosine active agent into association with the carrier. In general, the formulations are prepared by uniformly and intimately bringing the active agent into association with liquid carriers or finely divided solid carriers or both, and then shaping the product, if necessary. The invention extends to methods for preparing a pharmaceutical composition comprising bringing a compound of 2',3'-dideoxy-3'-C-hydroxmethylcytosine or its pharmaceutically acceptable salt in conjunction or association with a pharmaceutically acceptable carrier or vehicle. If the manufacture of pharmaceutical formulations involves intimate mixing of pharmaceutical excipients and the active ingredient is in a salt form, then it is often preferred to use excipients which are non-basic in nature, i.e. either acidic or neutral.

The formulations for oral administration of the present invention may be presented as discrete units such as capsules, cachets or tablets, each containing a predetermined amount of the active agent. Alternatively they can be presented as a powder or granules; as a solution or a suspension of the active agent in an aqueous liquid or a non-aqueous liquid, or as an oil-in-water liquid emulsion or a water-in-oil liquid emulsion, as a bolus, etc.

With regard to compositions for oral administration (e.g. tablets and capsules), the term "suitable carrier" includes vehicles such as common excipients, for example binding agents such as syrup, acacia, gelatin, sorbitol, tragacanth, polyvinylpyrrolidone (Povidone), methylcellulose, ethylcellulose, sodium carboxymethylcellulose, hydroxypropylmethyl-cellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredient. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

2',3'-dideoxy-3-C-hydroxymethyl-cytosine is synthesized by conventional nucleoside chemistries, such as those disclosed in U.S. Pat. No. 5,612,319, U.S. Pat. No. 5,473,063, Svansson L. et al. in J. org. Chem (1991) Vol 56: 2993-2997 and Björsne M. et al. in Tetrahedron, Vol 49: 8637-8644 (1993)

The synthesis of base-modified prodrugs, and certain conventional 3' and 5' esters is disclosed in Mauldin et al Biiorg Med Chem 6 (1998) 577-585.

The synthesis of 3' and 5' esters is typically carried out by reaction of the nucleoside (with the base N-protected with a conventional N-protecting group, as necessary) with the acid of the prodrug moeity:

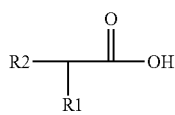

in conjunction with a conventional coupling reagent or with an activated derivative of this ester such as to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenyl derived esters and the like.

Regioselection of the 3' or 5' position, for those compounds comprising a single prodrug moiety is achieved with the use of bulky protecting groups, for examples as shown in WO97/30051, or using differentially selectable pairs of hydroxyl protecting groups as shown in Sanghvi et al. Synthesis 1994, 1163, Sanghvi et al Tett Lett vol 35 p 4697 (1994) and Haly & Sanghvi Nucleosides & Nucleotides Vol 15 1383 (1996).

Many pairs of differentially selectable hydroxyl protecting groups are known, for example the O-protecting groups disclosed in Greene, "Protective Groups In Organic Synthesis," (John Wiley & Sons, New York (1981)).

Hydroxy-protecting groups thus comprise ethers such as methyl ether or substituted methyl ethers, for example, methoxymethyl (MOM), benzyloxymethyl, t-butoxymethyl, 2-methoxyethoxymethyl (MEM), 2,2,2-trichloroethoxymethyl, bis(2-chloroethoxy)methyl, 2-(trimethylsilyl) ethoxymethyl, terohydropyranyl (THP), 3-bromotetrahydropyranyl, tetrahydrothiopyranyl, 4-methoxytetrahydropyranyl, 4-methoxytetrahydrothiopyranyl S,S dixido, tetrahydrofuranyl and tetrahydrothiofuranyl. Ethyl ethers include 1-ethoxyethyl, 1-methyl-1-methoxyethyl, 1-(isopropoxy)ethyl, 2,2,2-trichloroethyl and 2-(phenylselenyl)ethyl. Other ethers include t-butyl, allyl, cinnamyl, p-chlorophenyl and benzyl ethers such as unsubstituted benzyl, p-methoxybenzyl, o-nitrobenzyl, p-nitrobenzyl, p-halobenzyl and p-cyanobenzyl. Other ethers include 3-methyl-2-picolyl N-oxido, diphenylmethyl, 5-dibenzosuberyl, triphenylmethyl, alpha naphthyldiphenylmethyl, p-methoxy-phenyldiphenylmethyl, p(p'-bromophenacyloxy)phenyldiphenylmethyl, 9-anthryl, 9-(9-phenyl)xanthenyl, 9-(9-phenyl-10-oxo)anthryl (tritylone) and benzisothiazolyl S,S dioxodo. Silyl ethers include trimethylsilyl (TMS), triethylsilyl, isopropyldimethylsilyl, t-butyldimethylsilyl (TBDMS), (triphenylmethyl) dimethylsilyl, t-butyldiphenylsilyl, methyldiisopropylsilyl, methyldi-t-butylsilyl, tribenzylsilyl, tri-p-xylylsilyl, triisopropylsilyl and tripenylsilyl. Alternative hydroxyl protecting groups include esters, such as the formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, p-(P)-phenylacetate, 3-phenylpropionate, 3-benzoylpropionate, isobutyrate, monosuccinate, 4-oxopenatanoate (levinulate), pivaloate, adamantoate, crotonate, 4-methoxycrotonate, (E)-2-methyl-2-butenoate (tigloate) and benzoates such as the unsubstituted, or o-(dibromomethyl)-, o-(methoxycarbonyl)-, p-phenyl-, 2,4,6-trimethyl-(mesitate) or p-(P)-benzoates, or alpha-naphthoate. Carbonate hydroxyl protecting groups include the methyl, ethyl, 2,2,2-trichloroethyl, isobutyl, vinyl, allyl, cinnamyl, p-nitrophenyl, benzyls such as the unsubstituted, p-methoxy-, 3,4-dimethoxy-, o-nitro- or p-nitrobenzyls, or S-benzyl thiocarbonate. Miscellaneous hydroxyl protecting groups include N-phenylcarbamate, N-imidazolylcarbamate, borate, nitrate, N,N,N,N-tetramethylphosphorodiamidate and 2,4-dinitrophenylsulfenate. Greene provides extensive reactivity charts to facilitate is selecting complementary pairs of differential protecting groups.

Representative hydroxyl protecting groups include those in the examples, and ethers such as t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

Where necessary functional groups in the prodrug moiety such as NH, or the nucleoside base are protected and deprotected using conventional manipulation strategies, as shown for example in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoracetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

Synthesis of prodrugs of the monophosphate of 2',3'-dideoxy-3'-C-hydroxymethyl proceeds analogously to U.S. Pat. No. 5,756,711 U.S. Pat. No. 5,563,257, EP 545 966 and WO95/32984, with appropriate protection of the 3' hydroxymethyl function. Galenic formulations for such compounds are shown in WO97/26867.

DETAILED DESCRIPTION OF THE INVENTION

Various embodiments and aspects of the invention will now be described by way of example only, with reference to the accompanying examples and drawings.

Example 1

Activity of 2',3'-dideoxy-3-C-hydroxymethyl-cytosine against TAM primer rescue-related resistant HIV in the PhenoSense HIV assay The susceptibility of 2',3'-dideoxy-3'-C-hydroxymethyl-cytosine on HIV-1 isolates from patient plasma samples that bear typical TAM primer rescue mutant resistant genotypes is determined by the commercially available PhenoSense HIV assay (described in Petropoulos, C J et al., (2000) Antimicrob. Agents Chemother. 44:920-928 and performed by ViroLogics, Inc). The assay is performed by amplifying the protease (PR)-RT segment of the HIV pol gene from patient plasma and inserting the amplification products into a modified HIV-1 vector derived from an NL4-3 molecular clone.

Viral stocks are prepared by co-transfecting 293 cell cultures with recombinant viral DNA vector and an expression vector that produces the amphotropic murine leukemia virus envelope proteins. Pseudotyped virus particles are harvested from the transfected cell cultures and are used to infect fresh 293 cell cultures. The recombinant viral DNA contains a luciferase gene cassette within the HIV env gene region and the production of luciferase in target cells is dependent on the completion of one round of virus replication. Drug susceptibility is measured by adding serial concentrations of the compound of the invention and the reference compounds to the cells. Drugs that inhibit virus replication reduce luciferase signal in a dose-dependent manner, providing a quantitative measure of drug susceptibility.

Example 1a

Table 1 summarizes a main cluster of primer-rescue-related TAM mutants used in the experiment are resistant to HIV and bear the characteristic TAM genotype that typically emerges during AZT-involved antiretroviral therapy.

TABLE 1

Characteristic genotype in primer rescue-related
TAM patient isolates 20 and 21

| Isolate number | Characteristic primer rescue-related TAM mutations |
| --- | --- |
| 20 | M41L, D67N, K70R, V118I, L210W, R211K, T215F, K219Q and L228H |
| 21 | M41L, D67N, K70S, V118I, L210W, R211K, T215Y, K219N and L228H |

Figure 1:
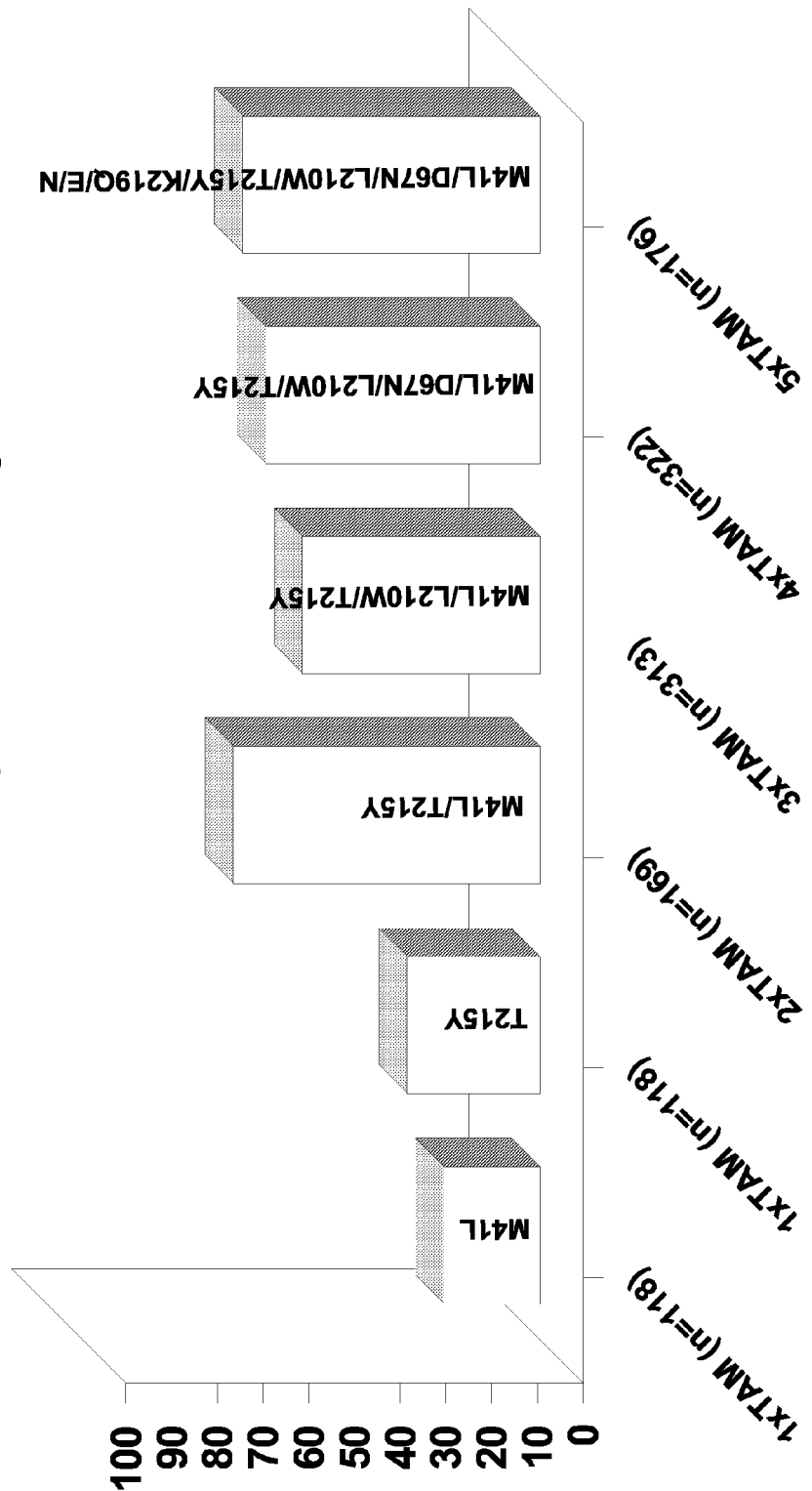
FIG. 1 is a graph depicting the prevalence of TAMs having a primer rescue phenotype in the M41L/L210W/T215Y background of 1086 RT sequences from virologic failure patients.
Figure 2:
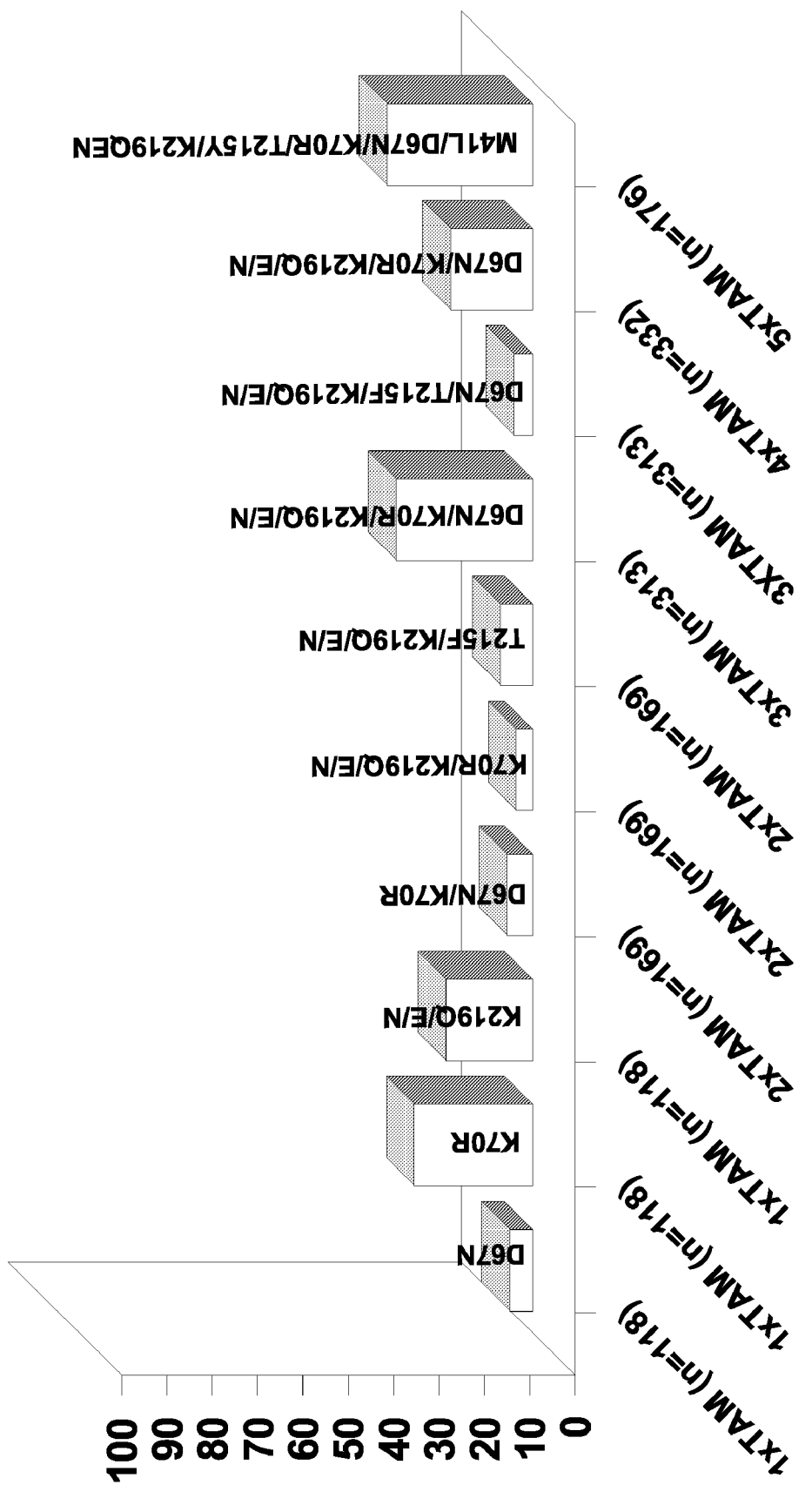
FIG. 2 is a graph depicting the prevalence of TAMs having a primer rescue phenotype in the D67N/K70R/L210W background of 1098 sequences from virologic failure patients.
Figure 3:
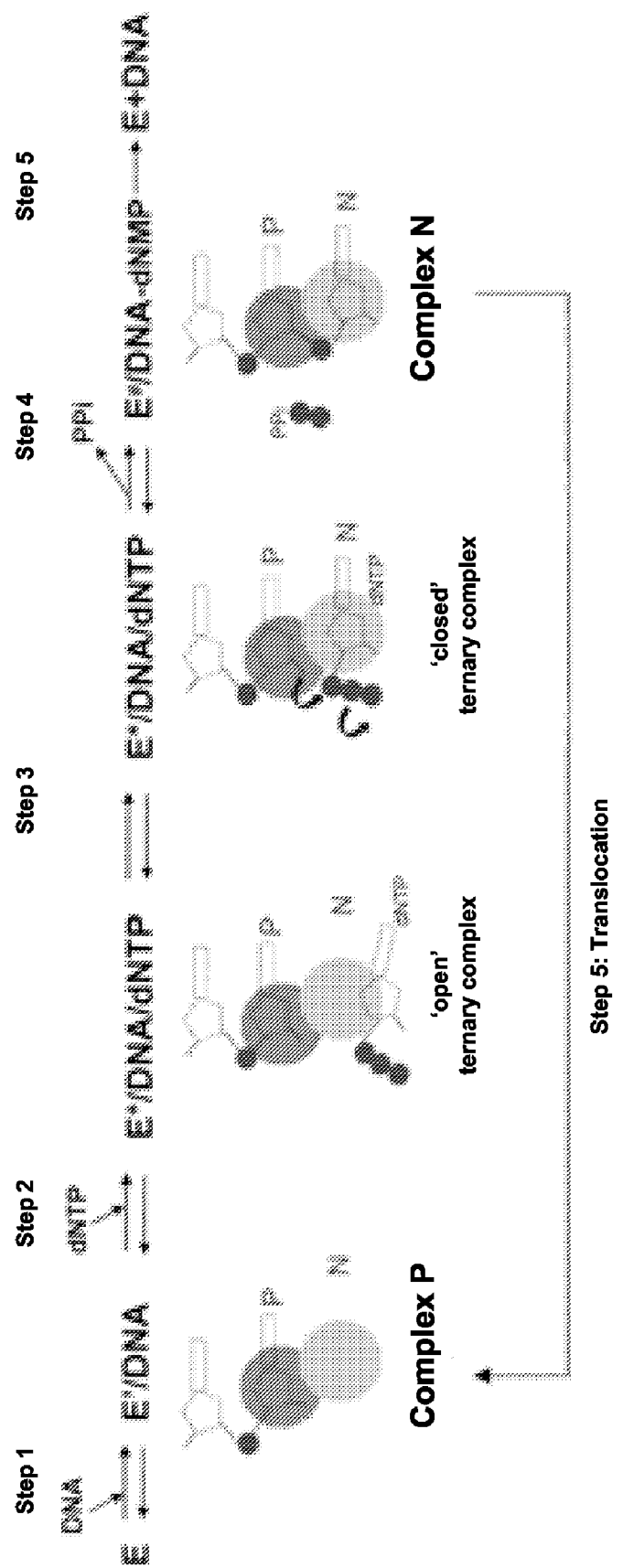
FIG. 3 is a schematic view of RT catalysed DNA polymerization.
Figure 4:
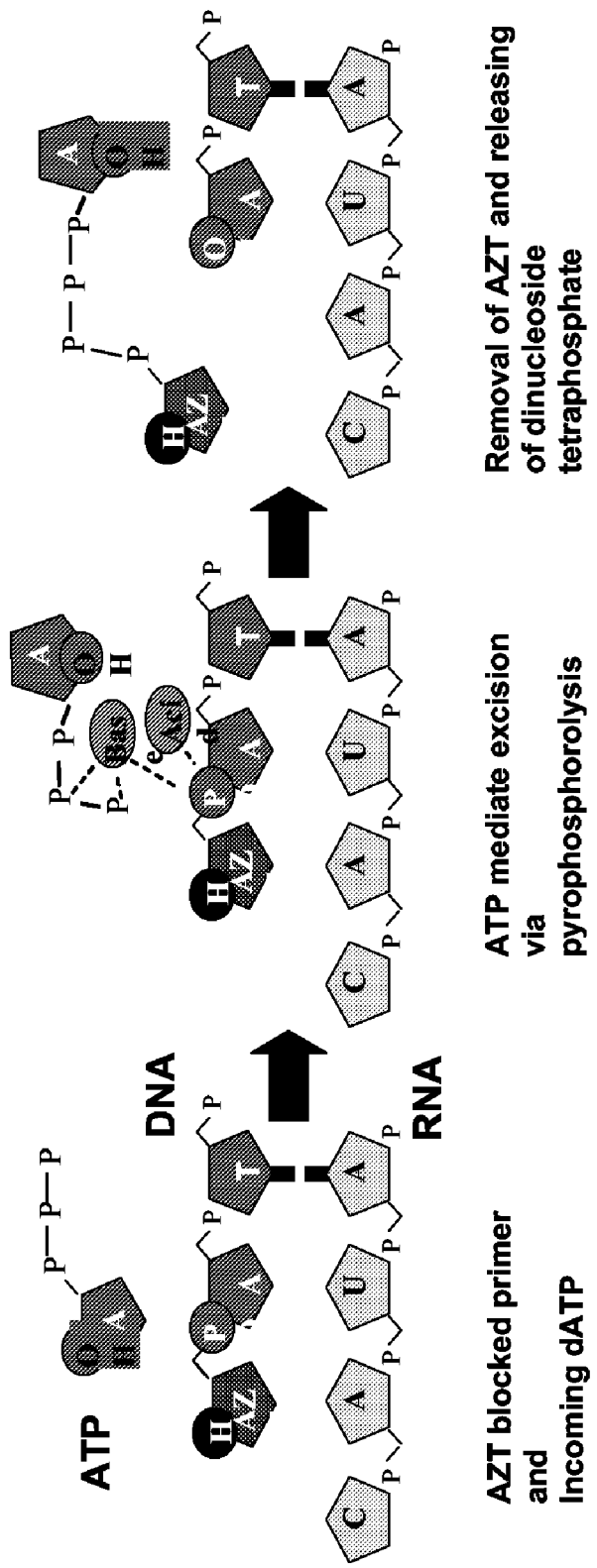
FIG. 4 is a schematic view of ATP-mediated primer rescue activity on an AZT-terminated primer terminus.
Figure 5:
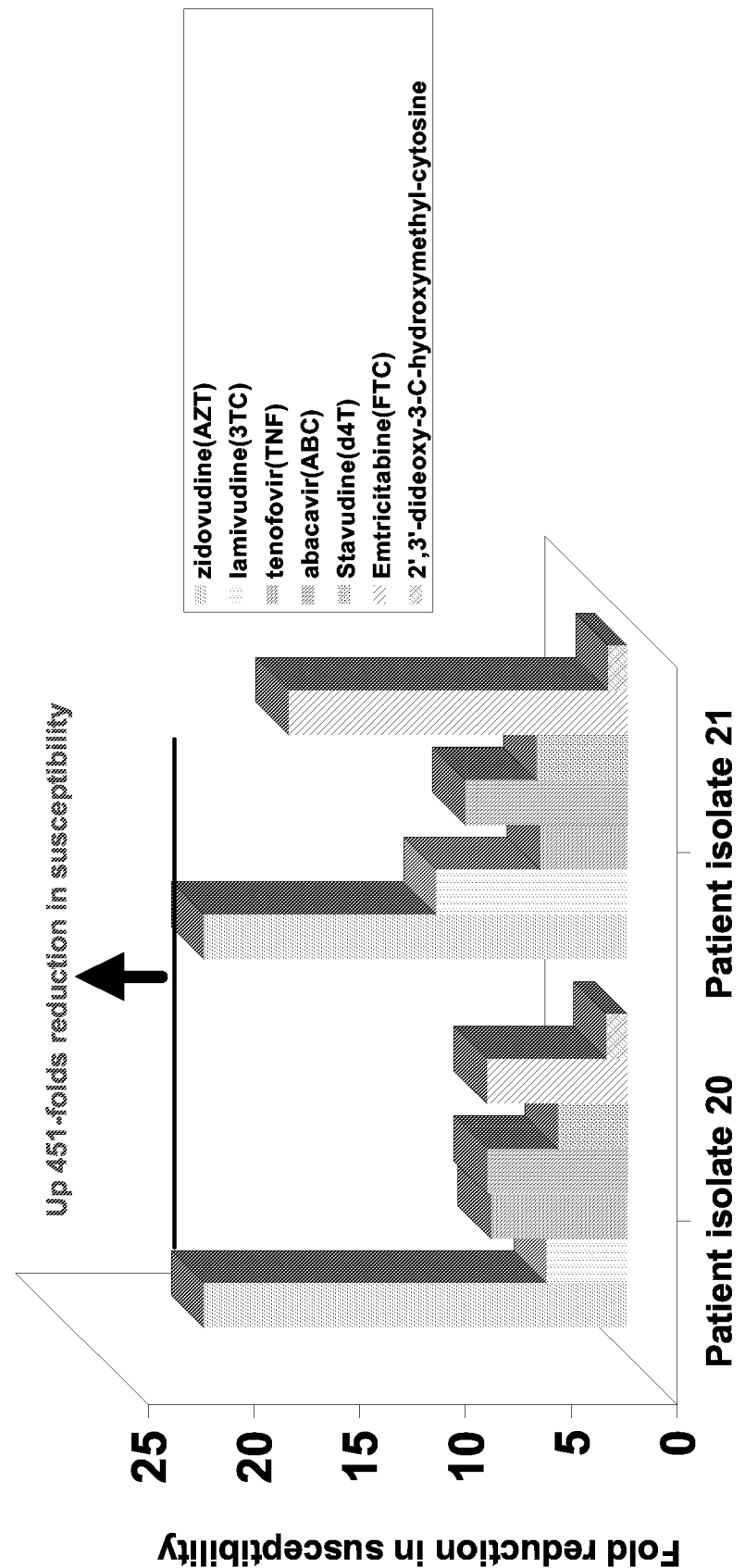
FIG. 5 depicts inhibition of typical TAM strains having a primer rescue phenotype by 2',3'-dideoxy-3-C-hydroxymethyl-cytosine, relative to inhibition of conventional NRTIs.

Results are depicted in FIG. 5. Wild-type HIV virus is used as the reference. Here, the inhibition of the patient isolate 20 and 21 strains is expressed as the fold change in reduction of susceptibility to the treatment drug as compared to parallel runs of the reference. The following antiviral drugs were tested: AZT, 3TC, TNF, ABC, d4T, FTC and the compound of the invention. It is clearly apparent that the invention's 2',3'-dideoxy-3'-C-hydroxymethylcytidine retained activity against the TAM bearing strains. The results show only a 1.0 fold reduction in susceptibility for the isolate 20 strain and less than a 1.0 fold reduction in susceptibility for the isolate 21 strain. This means that 2',3'-dideoxy-3'-C-hydroxymethylcytidine retained activity against the patient's primer rescue-related mutant HIV RT at a level of potency similar to its potency against wild type HIV RT. In contrast, other drugs, notably AZT (451 fold reduction in susceptibility), but also to 3TC, TFN, ABC, d4T and FTC, lost potency against the virus from these patients as compared to wildtype. In other words, the virus from these patients exhibited resistance, that is large reductions in susceptibility, to these drugs as shown in FIG. 5.

It is important to note that the two patient isolates harbor different amino acid transitions at codon 215; T to F in isolate 20 and T to Y in isolate 21. This is a representative hallmark of primer rescue-related TAM resistance mutants.

Example 1b

Table 2 outlines a primer rescue-related mutant HIV with the genetic background M184V (a discriminative mutant), which is typically selected by the very commonly employed antiretroviral therapy AZT+3TC (Combivir).

TABLE 2

Genotypic changes in TAM- primer
rescue-related patient isolate 19

| Isolate number | Characteristic primer rescue-related TAM mutations |
| --- | --- |
| 19 | M41L, D67N, K70R, V118I, M184V, L210W, T215F, K219E and L228H |

Figure 6:
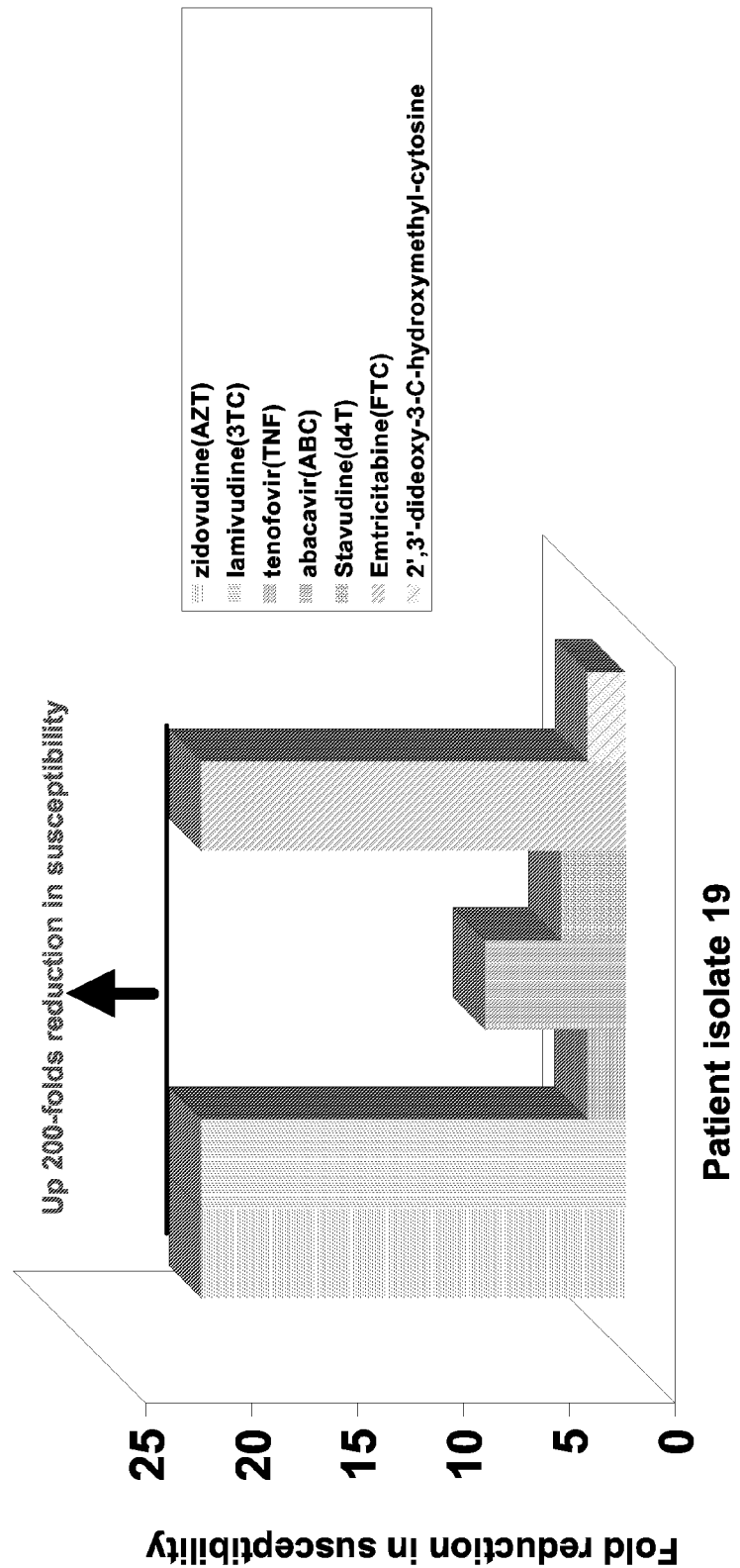
FIG. 6 depicts inhibition of M184V+TAMs having a primer rescue phenotype by 2',3'-dideoxy-3-C-hydroxymethyl-cytosine, relative to conventional NRTIs.
Figure 7:
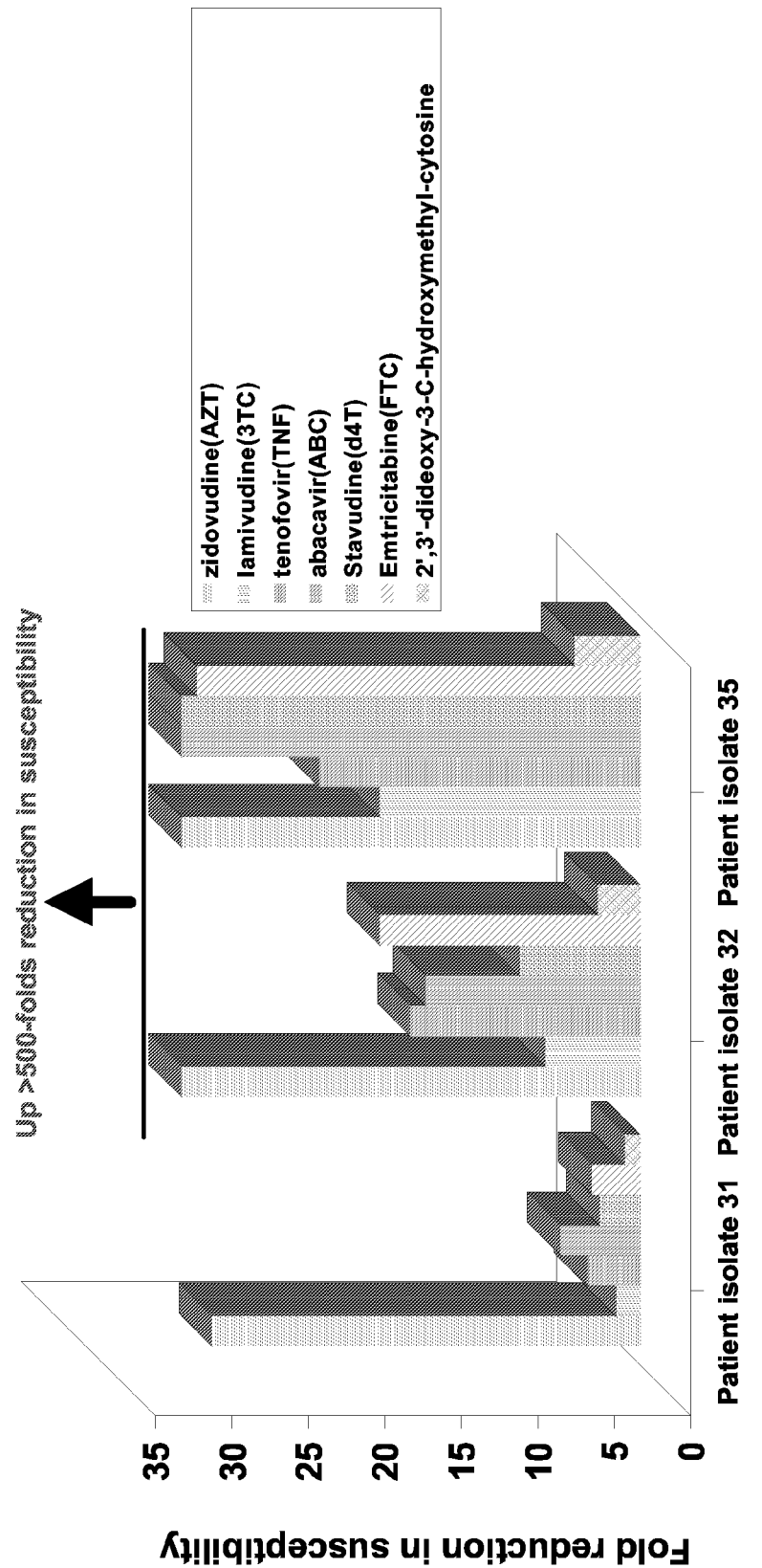
FIG. 7 depicts inhibition of T69S+XX+TAMs by 2',3'-dideoxy-3-C-hydroxymethyl-cytosine, relative to inhibition of conventional NRTIs.
Figure 8:
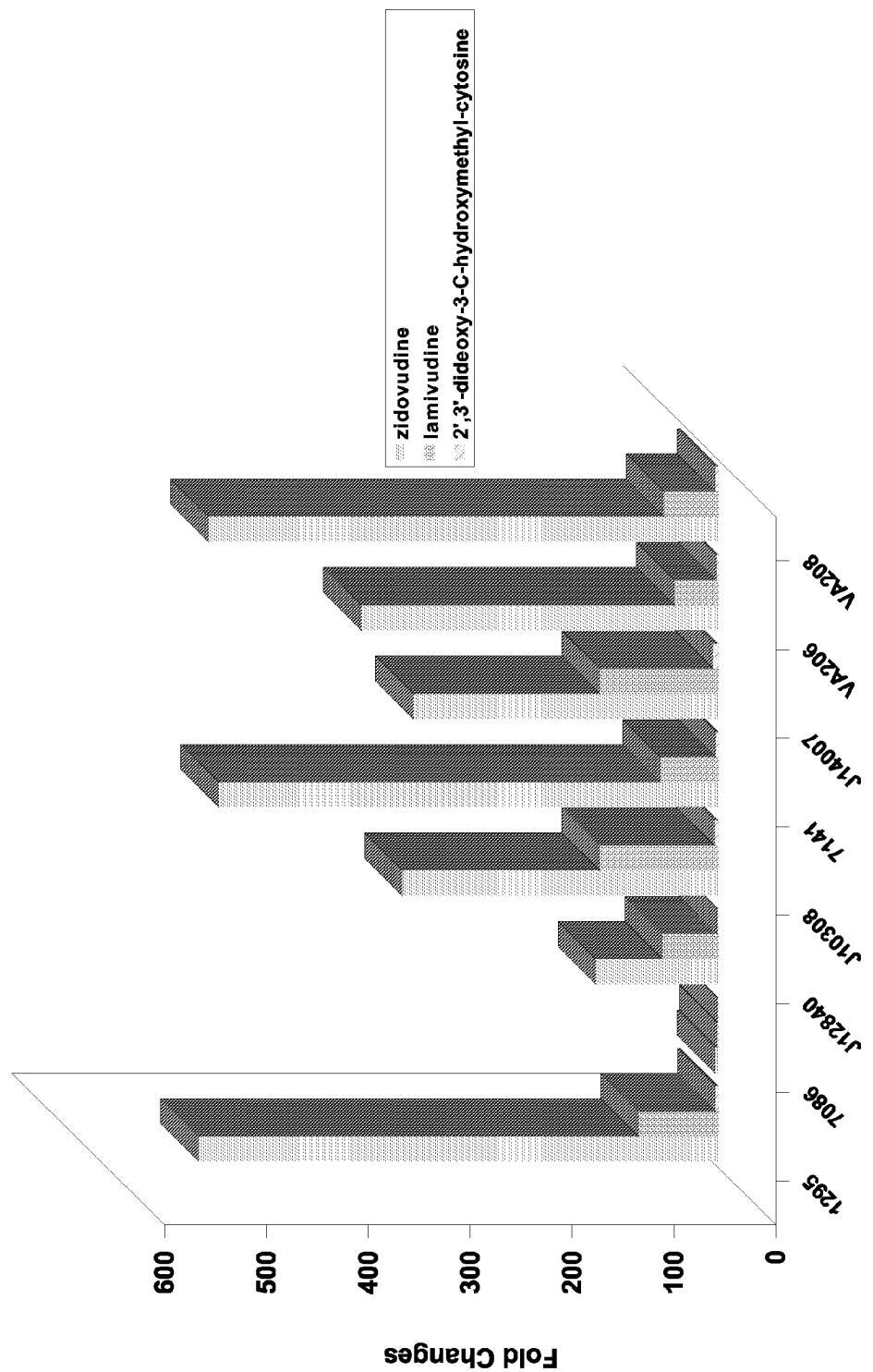
FIG. 8 depicts inhibition of TAM strains by 2',3'-dideoxy-3-C-hydroxymethyl-cytosine, relative to inhibition of zidovudine and lamivudine

As shown in FIG. 6, 2',3'-dideoxy-3'-C-hydroxymethylcytidine once again retained activity against this resistant virus, showing only a 1.78-fold difference in susceptibility compared to wild type HIV. Both 3TC and AZT lost activity and showed reduced potency (i.e. a pronounced reduction in viral susceptibility) to the resistance virus (FIG. 6).

Example 1c

Continuous challenge of patients with antiretroviral agents results in the emergence of MDR. A T69S mutation with a 6-bp insertion between amino acids 68 and 70 in the finger region of RT is often seen in combination with various forms of TAMs and contributes to an enhanced primer rescue activity. A cluster of MDR (with different forms of amino acid insertion(s)) in combination with TAM was chosen, as outlined in Table 3.

TABLE 3

Genotypic changes in primer rescue-related patient isolates 31, 32 and 35

| Isolate number | Characteristic primer rescue-related TAM mutations |
|---|---|
| 31 | T69S + double amino acid insertion SG in the genetic background of TAMs A62V, D67E and R211K |
| 32 | T69S + double amino acid insertion VG in the genetic background of TAMs A62V, D67G, V75I and T215I |
| 35 | T69S + double amino acid insertion VA in the genetic background of TAMs A62V, R211K, T215Y and L228H |

As shown in FIG. 7, the compound of the invention inhibited these patient isolates, giving the smallest change in drug susceptibility compared with six reference antivirals currently used in conventional antiretroviral therapy.

Note that a pronounced (500 to 1000-fold) reduction in susceptibility to AZT was observed for patient isolates 32 and 35 whereas the compound of the invention showed changes of 2.79 and 4.29-fold respectively. This is consistent with the compound of the invention displaying a different mechanism of inhibition compared to the obligatory DNA chain terminators represented by conventional NRTIs.

Example 1d

Isolate 4 represents a further discriminative mutant bearing the K65R+M184V genotype in a non-essential TAM background consisting of mutations at R211S and K219E. This isolate causes a typical cross-resistance to abacavir, 3TC and the newly approved nucleoside FTC, but retains its susceptibility to thymidine analogues, such as AZT and d4T. This isolate does not bear typical primer rescue mutations, yet the compound of the invention still inhibits this viral phenotype as indicated by an FC value of 3.88. This value is comparable to the thymidine analogues, AZT (FC=1.11) and d4T (FC=0.71), whereas significant resistance was found for 3TC (FC>200), FTC (FC>40) and to some extent to ABC (FC>9.0). This experimental data demonstrates that the compound of the invention not only bears unique properties against "primer rescue" mutants but is also able to inhibit HIV mutants from the discriminative family. This, therefore, contrasts with the inhibitory mechanism employed by 3TC and FTC as well as the likely mechanism of the Kodama 4'-C-ethynyl compounds described above in which M184V together with one additional amino acid change in codon T165R in the catalytic region contributes to cross-resistance to 4-C-ethynyl nucleoside (Kodama 2002).

Example 2

Activity of 2',3'-dideoxy-3-C-hydroxymethyl-cytosine against primer rescue-related resistant HIV in PBMC The antiviral performance of the compound of the invention against additional TAM primer rescue-related resistant HIV isolates was assayed in a PBMC culture. Isolates of HIV-1 were generated and expanded to high titer by co-cultivation of infected patient PBMC with PHA-stimulated donor PBMC (Virology Manual for ACTG HIV Laboratories). The cell-free supernatants were harvested, sequenced, and stored in aliquots at −70° C. for drug susceptibility assays.

In vitro drug susceptibility assays were performed using a modified ACTG/DOD consensus method (Virology Manual for ACTG HIV laboratories). PBMCs were pre-infected with viral stocks for 4 hrs at 3TC in a humidified atmosphere of 5% $CO_2$ following 4 hr incubation. Infected cells were washed twice in media and pipetted into a microtiter plate with eight serial drug dilutions. Each well contained 100,000 pre-infected PBMC and all drug dilutions were made with cell culture medium. The drug dilutions were chosen to span the 50% inhibitory concentration ($IC_{50}$) for each single drug. Control wells containing cells and virus were co-incubated on each plate. After a 7-day incubation at 3TC in a mummified atmosphere of 5% $CO_2$, viral growth was determined using a p24 antigen assay on supernatants (Abbott Laboratories, Chicago, USA). The percent inhibition of viral growth compared to the control well, which contained no drug, was calculated and expressed as fold changes (reductions in compounds susceptibility) compared to the control well. The reference compound AZT was run in parallel with the compound of the invention.

A cluster of representative of primer rescue-related mutant virus was selected that harbors the essential feature of primer rescue-related TAM resistant RT mutations. Strains with mutations at position M41L, D67N, K70R, L210W, T215Y/F and K219Q/E in various combinations with or without discriminative mutant M184V were used as indicated in Table 4.

TABLE 4

TAM primer rescue-related genotype in 9 patient isolates

| Isolate number | Characteristic primer rescue-related TAM mutations |
|---|---|
| 1295 | M41L, D67N, K70R, V75M, V118I, M184V, L210W, R211K, T215Y and K219E |
| 7086 | D67N, T69N, K70R, V118I, L210W, T215V and K219Q |
| J12840 | M41L, D67N, V118I, M184V, L210W, R211N, T215Y |
| J10308 | M41L, D67N, M184V, L210W, R211S, T215Y |
| 7141 | M41L, D67N, M184V, H208Y, R211K, T215Y, K219N |
| J14007 | D67N, T69N, K70R, M184V, H208Y, R211K, J215F, K219Q, L228H |
| VA206 | D67N, M184V, L210W, R211K, T215Y |
| VA286 | M41L, E44D, D67N, L74V, V118I, M184I, E203K, H208Y, L210W, R211K, T215Y |

Most of these selected primer rescue mutants conferred a pronounced resistance to AZT susceptibility, dropping a couple of hundred folds in FC value. The exception was isolate 7086 (FC=3.0), which bears the T215V amino acid mutation. A complete report of FC values is presented in FIG. 8. Here, 2',3'-dideoxy-3'-C-hydroxymethylcytidine inhibited all 8-isolates, with the highest FC value being only 2.7.

Example 3

2',3'-dideoxy-3'-C-hydroxymethylcytidine retains the ability to support DNA synthesis The presence of a 3'-hydroxymethyl group in the compound of the invention should, in principle, support incorporation and elongation into the viral nucleic acid catalyzed by HIV-1 RT. A rate-limiting amount of primer-template (16S and 23S ribosomal RNA annealed with an oligo-DNA primer with the sequence of 5'-TAACCTTGCGGCCGT-3' (SEQ ID NO:1), custom synthesized by INNOVAGEN) was used. This was pre-incubated with 100 μM (55 times the $IC_{50}$) 2'-3'-dideoxy-3'-C-hydroxymethylcytidine-triphosphate, 6.0 μM ddC-triphosphate (54 times the $IC_{50}$ ddCTP), 20 μM deoxycytosine-triphosphate (20 times the Km dCTP) or the control ($H_2O$). At the time points indicated (0, 10, 30, 60, and 120 min), the DNA polymerization process was stopped by inactivation of the RT at 70° C. for 2 min during the first round of DNA polymerization (FIG. 9).

The residual amount of primer-template directly reflects the availability of free 3'-OH primer terminus present after the first round of reaction. In order to measure this, a new polymerization was initiated by addition of fresh RT in the presence of 150 μM (160 times the Km) dCTP and tritium-labeled dCTP which is sufficient to compete out any inhibitory effect from the residual 2'-3'-dideoxy-3'-C-hydroxymethylcytidineTP and ddCTP that is left from the first round of DNA polymerization. The availability of free 3'-OH at the primer terminus in the residual amount of primer-template that supported further DNA polymerization was measured and expressed as a function of pre-incubation time (FIG. 10).

Figure 9:
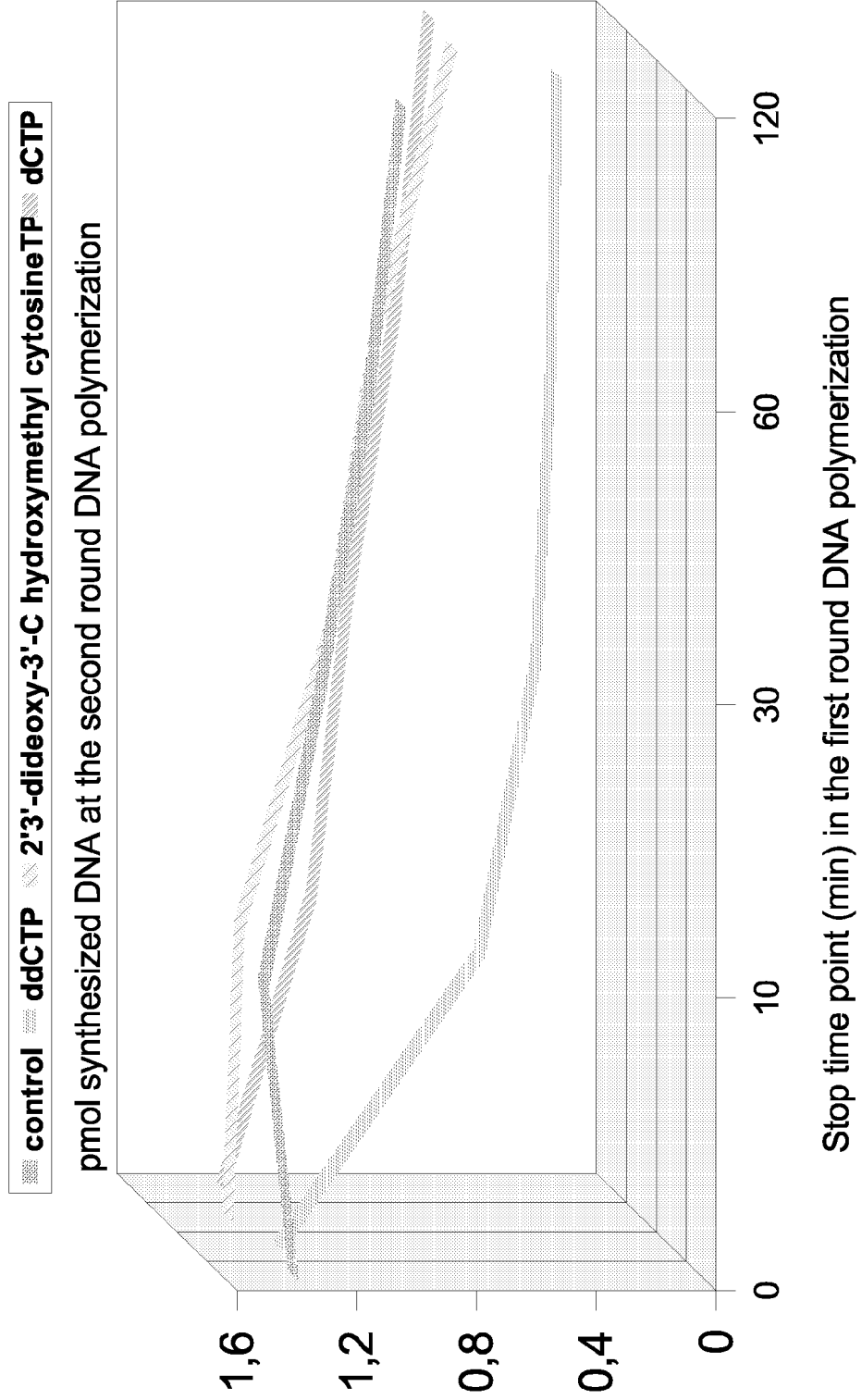
FIG. 9 is a graph depicting the synthesis of DNA as a function of time, reflecting incorporation of 2'3'-dideoxy-3'-C hydroxymethyl cytosine monophosphate.
Figure 10:
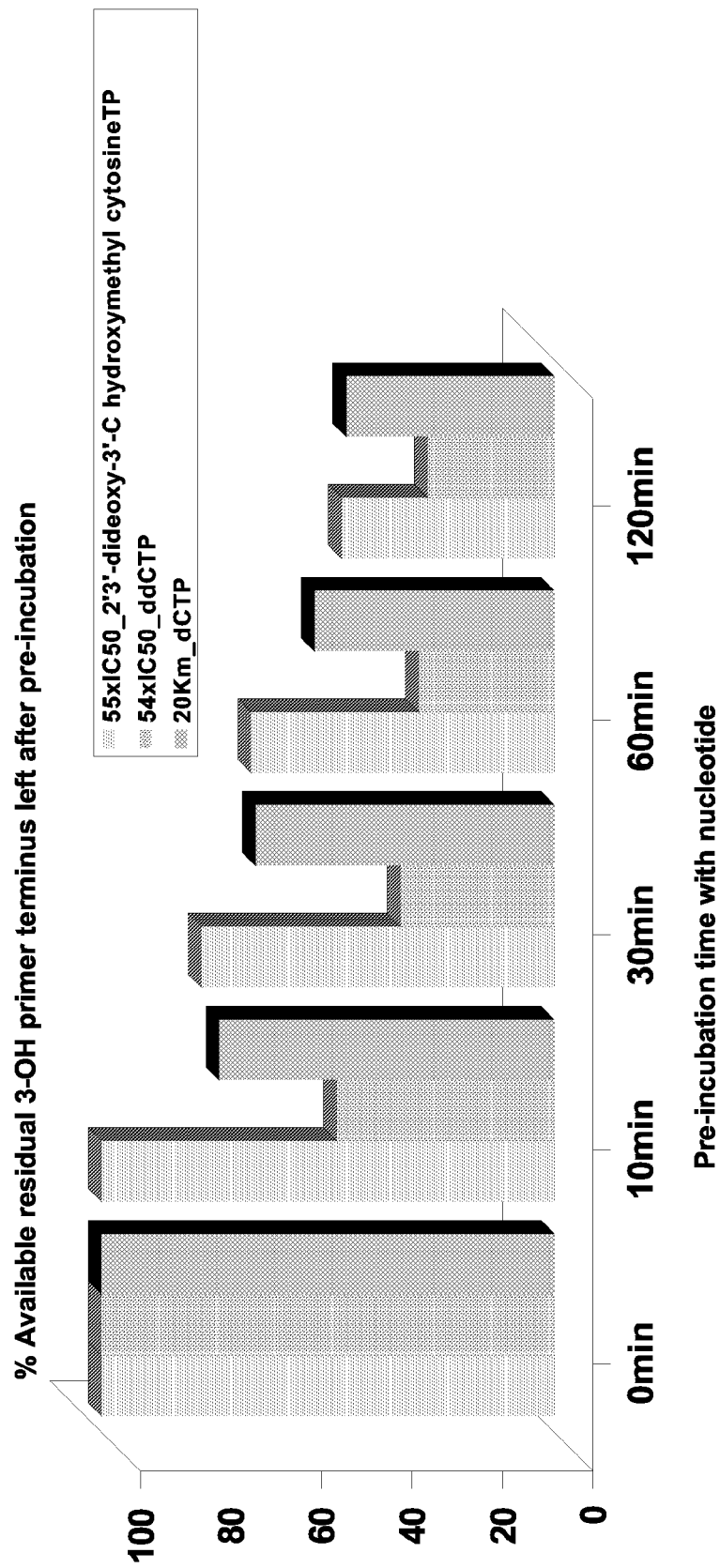
FIG. 10 is a graph depicting residual 3'-OH primer, indicating that incorporation of 2',3'-dideoxy-3'-C-hydroxymethylcytidine allows limited further DNA synthesis.

With reference to FIGS. 9 & 10, although ddCTP and 2'3'-dideoxy-3'-C-hydroxymethylTP were set to provide an equal inhibitory level, there was a sharp contrast in their respective ability to support the second round of HIV RT-catalyzed DNA polymerization. Pre-incubation with an obligatory chain terminator such as ddCTP causes chain termination and gives a significant reduction of free 3-OH primer terminus compared to the triphosphate of the compound of the invention. At pre-incubation time points of 10 and 30 minutes, less than half the amount of residual 3-OH primer terminus was left to support further DNA prolongation when ddCTP is present compared to the triphosphate of the compound of the invention, notwithstanding that comparable amounts of the TP compounds were used in the first round of DNA polymerization. This clearly indicates that the incorporation of the TP of the compound of the invention into the nascent nucleic acid provides continued opportunity for some further DNA synthesis. The DNA polymerization must include binding of the enzyme to the template, complex with appropriate dNTP, phospho-diester formation, liberation of pyrophosphate and translocation of the enzyme from the N-site into the P-site in order for the next round of synthesis to occur. It is therefore apparent that the compound of the invention is able to be incorporated and translocated by the enzyme into the next position, after which further elongation ceases.

Example 4

Incorporation of 2',3'-dideoxy-3'-C-hydroxymethylcytidine monophosphate leads to a different chain termination pattern compared to ddC Two deoxycytosine analogues, the conventional NRTI ddC lacking a 3'-hydroxyl group function and the compound of the invention, were subjected to a DNA chain termination assay in which DNA prolongation was conducted with M13mp18 single strand DNA template pre-annealed to an oligo-DNA primer (the forward primer sequence of 5'-GTTTTCCCAGT-CACGACGTTGTA-3' (SEQ ID NO:2) was purchased from Amersham UK. M13mp18 single strand RNA was annealed to this oligo-DNA primer giving a final concentration of 1 mg/ml in a buffer containing 10 mM Tris-HCl, pH 7.9 and 100 mM NaCl, and was stored in aliquots at −20° C. DNA polymerization was conducted using this annealed template/primer, HIV-1 RT and natural dNTPs in a reaction incubated at 37° C. for 25 min. The reaction was stopped by the addition of Stop solution containing 95% Formamide, 20 mM EDTA, 0.05% Bromophenol Blue and 0.05% Xylene Cyanol FF (purchased from USB, United States Biochemical via Amersham UK). After denaturing the DNA products, the elongated DNA fragment was electrophoresed on an 8.0% polyacrylamide gel and visualized using autoradiography.

The assay included a negative control (the native dNTP), dual positive ddCTP controls (ddCTP, 8 uM from Sigma Chemical, St. Louis, Miss., USA and ddCTP obtained from a USB sequence kit United States Biochemical via Amersham UK). Various molecule ratios of the triphosphate of the compound of the invention and the natural dNTP were used. After the reaction was conducted as described above, the denatured DNA fragments from each individual reaction was loaded onto an 8.0% polyacrylamide gel in the following order:

1—Negative control
2—$1^{st}$ Positive control 8 μM ddCTP (purchased from Sigma)
3—20 μM inventionTP in 200 μM dNTP
4—30 μM inventionTP in 300 μM dNTP
5—40 μM invention TP in 400 μM dNTP
6—50 μM invention TP in 500 μM dNTP
7—20 μM invention TP in 80 μM dNTP
8—40 μM invention TP in 80 μM dNTP
9—Empty space (no loading)
10—$2^{nd}$ positive control ddCTP (from USB sequence kit)

Figure 11:
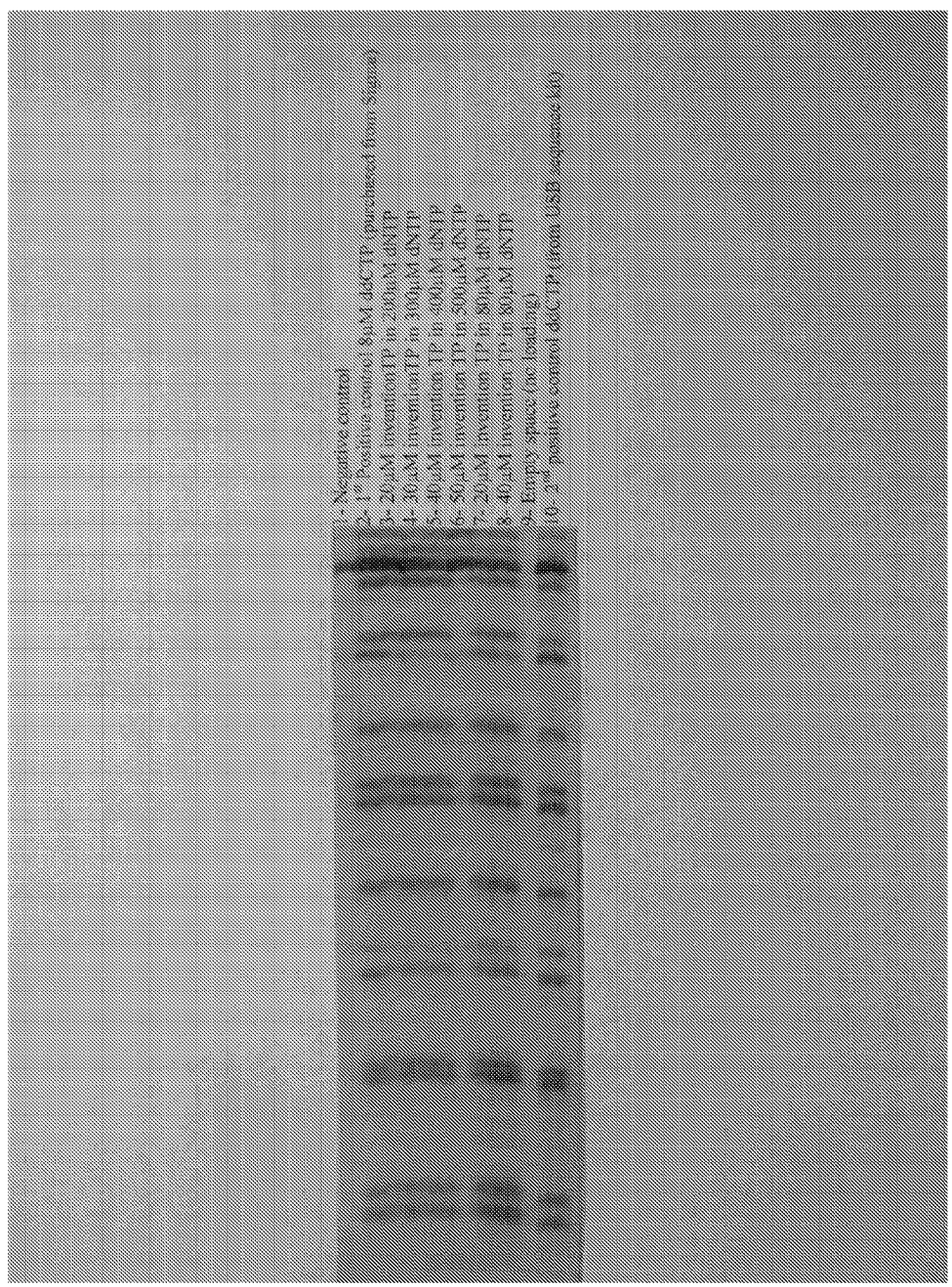
FIG. 11 is an autoradiograph of a gel showing that 2',3'-dideoxy-3'-C-hydroxymethylcytidine monophosphate induced chain termination differs from ddC monophosphate induced chain terminated DNA. The ddC monophosphate induced chain terminated DNA fragment appears lower in the gel than the fragment produced using the compound of the invention.

In order to avoid any other factor which may influence interpretation of assay outcome, such as the edge effect associated with polyacrylamide gels, a duplicate set of samples were loaded in the middle of the gel. FIG. 11 shows a digital photo from depicting autoradiology results obtained from the central part of the gel:

1. Negative control (dNTP): no pause in DNA polymerization was found.
2. $1^{st}$ positive control 8 μM ddC-TP: led to chain termination at the anticipated 2'3'-deoxydeoxycytosine sites.
3. 20μ inventionTP/200 μMdNTP: led to chain termination at the site after/behind 2'3'-deoxydeoxycytosine site.
4. 30 μM inventionTP/300 μMdNTP: led to chain termination at the site after 2'3'-deoxydeoxycytosine site compared to ddC-TP.
5. 40 μM inventionTP/400 μMdNTP: lead to chain termination at the site after 2'3'-deoxydeoxycytosine site compared to ddC-TP.
6. 50 μM inventionTP/500 μMdNTP: No specific pause (chain termination pattern) was found, but is considered to be within experimental error.
7. 20 μM inventionTP/80 μMdNTP: led to a more pronounced chain termination effect at the site after the 2'3'-deoxydeoxycytosine site compared to ddC-TP and the invention experimental sample intermediately above.
8. 40 μM inventionTP/80 μMdNTP: led to a more pronounced chain termination effect at the site after the 2'3'-deoxydeoxycytosine site compared to ddC-TP and the invention experimental sample intermediately above.

9. Empty space (no sample loaded)
10. $2^{nd}$ positive control ddC-TP: led to chain termination at anticipated 2'3'-deoxydeoxycytosine sites.

The compound of the invention has induced DNA chain termination in all samples, with the exception of the sample no. 6 which contains 50 µM of the invention's TP in 500 µM dNTP. The reason for this exception is unknown, but is likely within experimental error. Interestingly, DNA fragments resulting from incorporation of 2',3'-dideoxy-3'-C-hydroxymethylcytidine monophosphate migrate more slowly than those resulting from the two positive control ddCTP terminated DNA fragments (FIG. 11). The duplicated reactions show a consistent pattern which implies that the compound of the invention is incorporated into the newly synthesized DNA strand and allows the formation of a further 3',5'-phosphodiester bond in the next round of nucleotide incorporation. Although a fragment longer by one base was observed, it cannot be excluded that the sequence of the template employed may play a role.

the RT molecule to undergo the necessary transformational change in order to prepare for the next round of DNA synthesis. Examples 3 and 4 have clearly demonstrated that the compound of the invention bears such properties and thus it is able to defeat/counteract the primer rescue resistant mechanism as demonstrated in Examples 1 and 2.

Sarafinano et al. (2002 and 2003) provide compelling experimental data supporting the conclusion that the primer rescue reaction can only occur before RT translocates into the next position. That is, the pre-translocation complex is a prerequisite condition for a primer rescue mutant to be effective. The evidence presented in the Examples suggests that is not the case for the compound and methods of the current invention.

Example 5

Preparation of ester prodrugs releasing 2',3'-dideoxy-3-'C-hydroxymethylcytidine

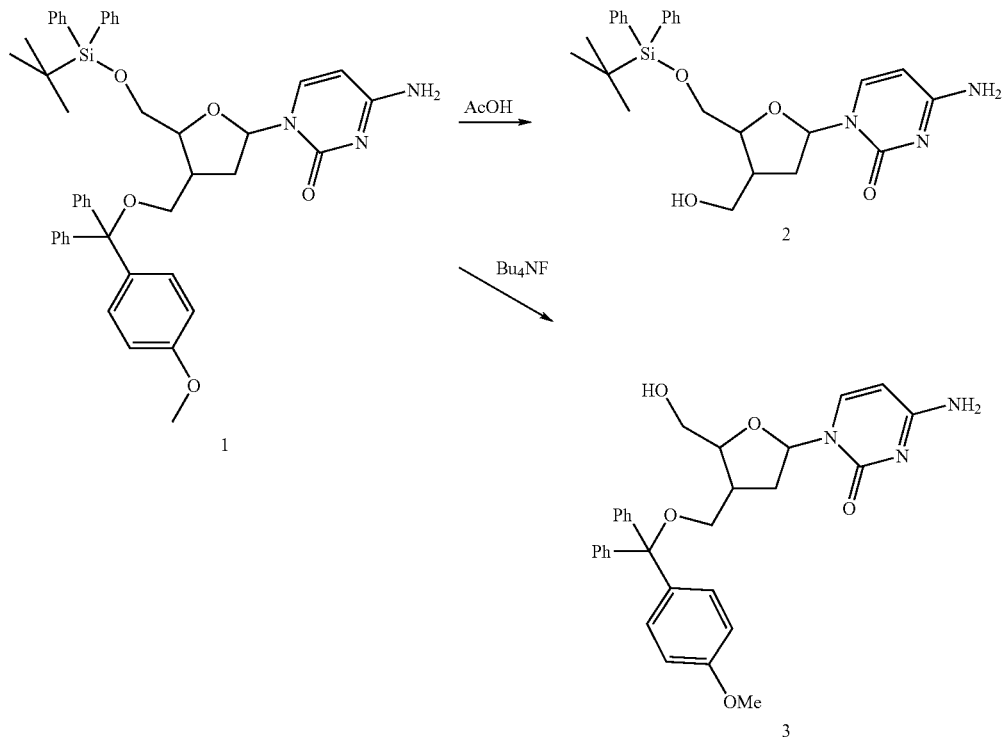

Example 3 clearly shows that the 3'-OH primer terminus which was pre-terminated by the compound of the invention supports further nucleotide incorporation more than a ddCTP pre-terminated 3'-OH primer terminus, when a ribosomal RNA template is used. This feature causes the slow electrophoresis mobility and implies that the RT has undergone translocation to begin the next round of polymerization.

Although not wishing to be bound by this mechanism, it is believed that the compound of the invention therefore represents a new strategy in inhibiting primer excision mutants. That is the compound is incorporated into the growing viral genome while simultaneously retaining the ability to allow Preparation of Compound 1:
The 3'-MMTR/5'-TMBDS differentially protected Compound 1 is prepared as the corresponding uridine as described by Sanghvi et al: Synthesis (1994) p1163 & Tetrahedron Lett v35 (1994) p4697 & Nuclesoides & Nucleotides v15 (1996) 1383. The U to C conversionis shown in Kozlov et al Nucleosides & Nucleotides, v17 (1998) 2249.

Preparation of Compound 2:
Compound 1 (5.0 g, 6.7 mmol) was dissolved in 80% acetic acid (30 mL) and stirred for 24 h at room temperature. The mixture was evaporated and the product was purified by flash chromatography 5 to 10% MeOH in $CH_2Cl_2$ as eluent. The yield 2.1 g (64%).

Preparation of Compound 3:
Compound 1 (2.3 g, 3.06 mmol) in THF (150 mL) was treated with Tetrabutylammonium fluoride (1M in THF, 3.0 mL) for 1 h at room temperature. Sodium bicarbonate (sat, 100 mL) was added and the mixture was extracted with dichloromethane (3×50 mL). The organic layer was dried and evaporated. The residue was purified by flash chromatography to give 1.3 g (82%) of compound 3.
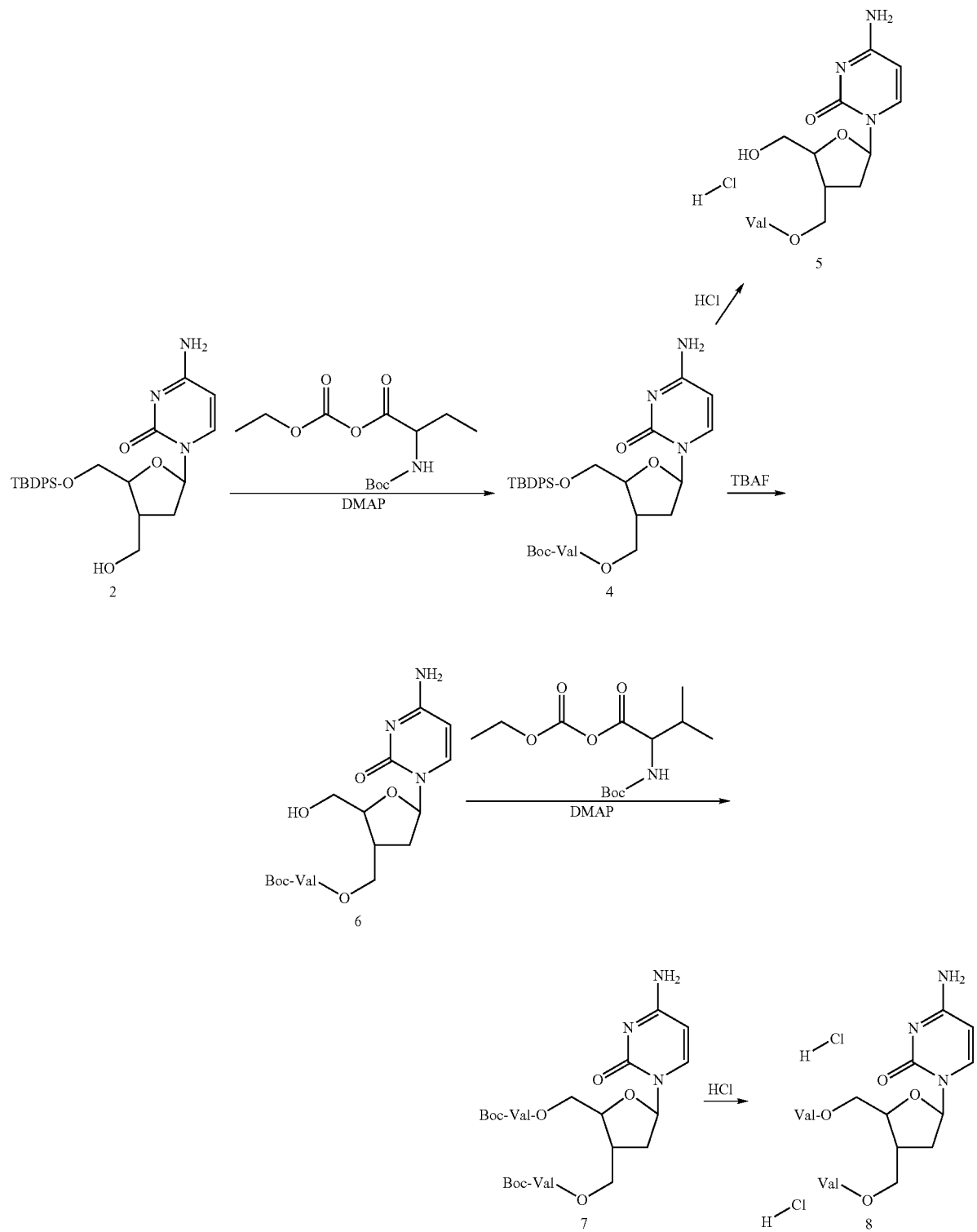
Scheme 2

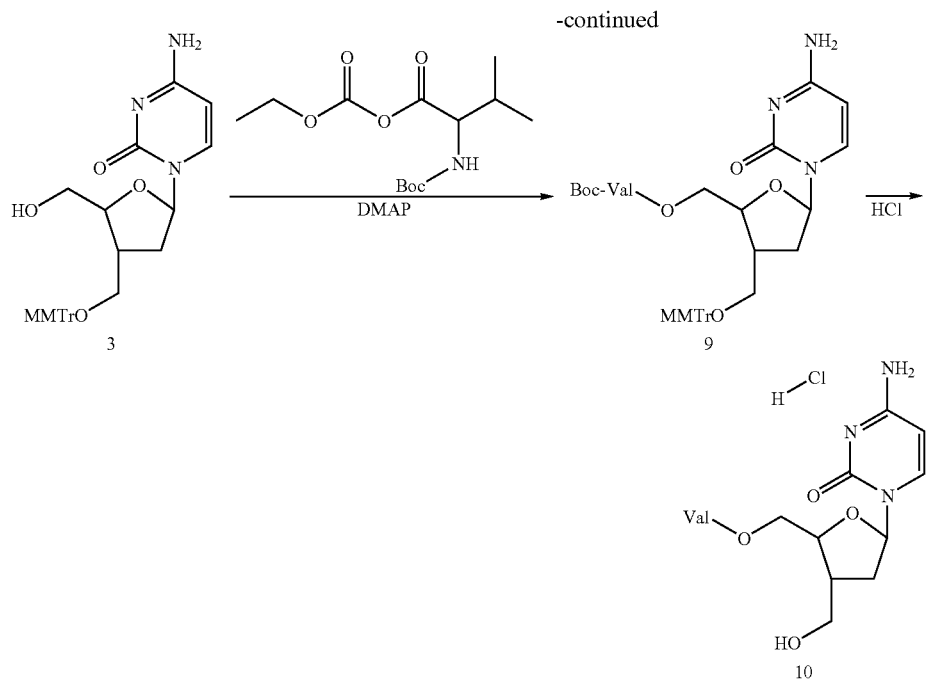

Preparation of Compound 4:

Triethylamine (0.455 g, 4.5 mmol) and Ethyl chloroformate (0.26 g, 2.4 mmol) were added to the solution of Boc-Valine (0.49 g, 2.25 mmol) in THF (15 mL) at 0° C. The reaction mixture was stirred for 3 h at same temperature and then filtrated to the solution of Compound 2 (0.72 g, 1.5 mmol) and DMAP (0.55 g, 4.5 mmol) in THF (15 mL). The reaction mixture was stirred overnight at room temperature. EtOAc was added to the mixture and it was washed three times with 2% citric acid and once with sat. NaHCO$_3$. The organic layer was dried over Na$_2$SO$_4$, filtrated and evaporated. The residue was purified by flash chromatography 2 to 5% MeOH in CH$_2$Cl$_2$ as eluent to give 0.35 g (34%) of Compound 4.

Preparation of Compound 5:

Compound 4 (30 mg, 0.066 mmol) was dissolved in conc. HCl (1 mL) at room temperature and stirred for 5 min. Acetone was added to the solution and it was evaporated. Acetone was added again and the solution was evaporated and dried under vacuum to give 18 mg (69%) of Compound 5.

Preparation of Compound 6:

Compound 4 (0.35 g, 0.5 mmol) was dissolved in THF (20 mL) and 1.0 M Tetrabutylammonium fluoride in THF (0.5 mL, 0.5 mmol) was added. The reaction mixture was stirred for 2 days at room temperature. The mixture was evaporated and the product was purified by flash chromatography 5 to 10% MeOH in CH$_2$Cl$_2$ as eluent to give 0.225 g (98%) of Compound 6.

Preparation of Compound 7:

The synthesis was made in the same manner as for the Compound 4 using Compound 6 as starting material.

Preparation of Compound 8:

Compound 7 (75 mg, 0.114 mmol) was dissolved in 3 mL of MeOH and conc. HCl (0.5 mL) was added at 0° C. The mixture was stirred for 5 min at 0° C. and for 3 min at room temperature and after that evaporated. Acetone was added to the residue and it was evaporated. CH$_2$Cl$_2$ was added and the residue was evaporated and dried under vacuum to give 58 mg (96%) of Compound 8.

Preparation of Compound 9:

Ethyl chloroformate (110 mg, 1.0 mmol) was added to the solution of Boc-Valine (220 mg, 1.0 mmol) and trithylamine (200 mg, 2.0 mmol) in THF (30 mL) at 0° C. and the mixture was stirred for 3 h. The temperature was allowed to reach room temperature and the mixture was filtered. The filtrate was added to the solution of compound 3 (350 mg, 0.68 mmol) and DMAP (244 mg, 2.0 mmol) in THF (20 mL). The reaction mixture was stirred overnight at room temperature, ethyl acetate (100 mL) was added to the mixture and it was washed with citric acid (10%, 2×30 mL) and sodium bicarbonate (sat, 30 mL). Solvent was removed and the product was separated on silica gel column to give compound 9 (220 mg, 45%).

Preparation of Compound 10:

Compound 9 (200 mg, 0.28 mmol) was dissolved in 3 mL of conc. HCl and stirred for 3 min at room temperature. The mixture was evaporated, washed with acetone, acetonitrile and diethyl ether and dried under vacuum to give 85 mg (77%) of Compound 10.

Preparation of Compound 11:

Ethyl chloroformate (110 mg, 1.0 mmol) was added to the solution of Boc-Valyl-Lactic acid (290 mg, 1.0 mmol) and triethylamine (200 mg, 2.0 mmol) in THF (30 mL) at 0° C. and the mixture was stirred for 3 h at 0° C. The temperature was allowed to reach room temperature. The mixture was filtered and the filtrate was added to the solution of compound 3 (300 mg, 0.58 mmol) and DMAP (244 mg, 2.0 mmol) in THF (20 mL). The reaction mixture was stirred overnight at room temperature, ethyl acetate (100 mL) was added to the mixture and it was washed with citric acid (10%, 2×30 mL) and sodium bicarbonate (sat, 30 mL). Solvent was removed and the product was separated on silica gel column to give compound 11 (250 mg, 38%).

Preparation of Compound 12:

The compound was prepared from Compound 11 in the same manner as Compound 8.

Preparation of Compound 13:

The compound was prepared in the same manner from Compound 2 as Compound 4 by using Boc-Valyl-Lactic acid as starting material instead of Boc-Valine.

Preparation of Compound 14:

The synthesis was made from Compound 13 as for Compound 10.

Preparation of Compound 15:

Compound 1 (1 g, 1.33 mmol) was dissolved in 14 mL of conc. HCl and the mixture was stirred for 8 min at room temperature and then evaporated. The residue was washed with acetone and filtrated to give 334 mg (90%) of Compound 15.

Preparation of Compound 16:

Triethylamine (0.487 g, 4.82 mmol) and Ethyl chloroformate (0.30 g, 2.77 mmol) were added to the solution of Boc-Valine-Lactic acid (0.77 g, 2.65 mmol) in THF (30 mL) at 0° C. The reaction mixture was stirred for 3 h at same temperature and then filtrated to the solution of Compound 15 (0.334 g, 1.20 mmol) and DMAP (0.74 g, 6.0 mmol) in THF (30 mL) and DMF (30 mL). The mixture was stirred overnight at room temperature. EtOAc was added to the mixture and it was washed three times with 2% citric acid and once with sat. NaHCO$_3$. The organic layer was dried over Na$_2$SO$_4$, filtrated and evaporated. The crude product was purified by flash chromatography 2 to 5% MeOH in CH$_2$Cl$_2$ as eluent to give only 65 mg (8%) of Compound 16.

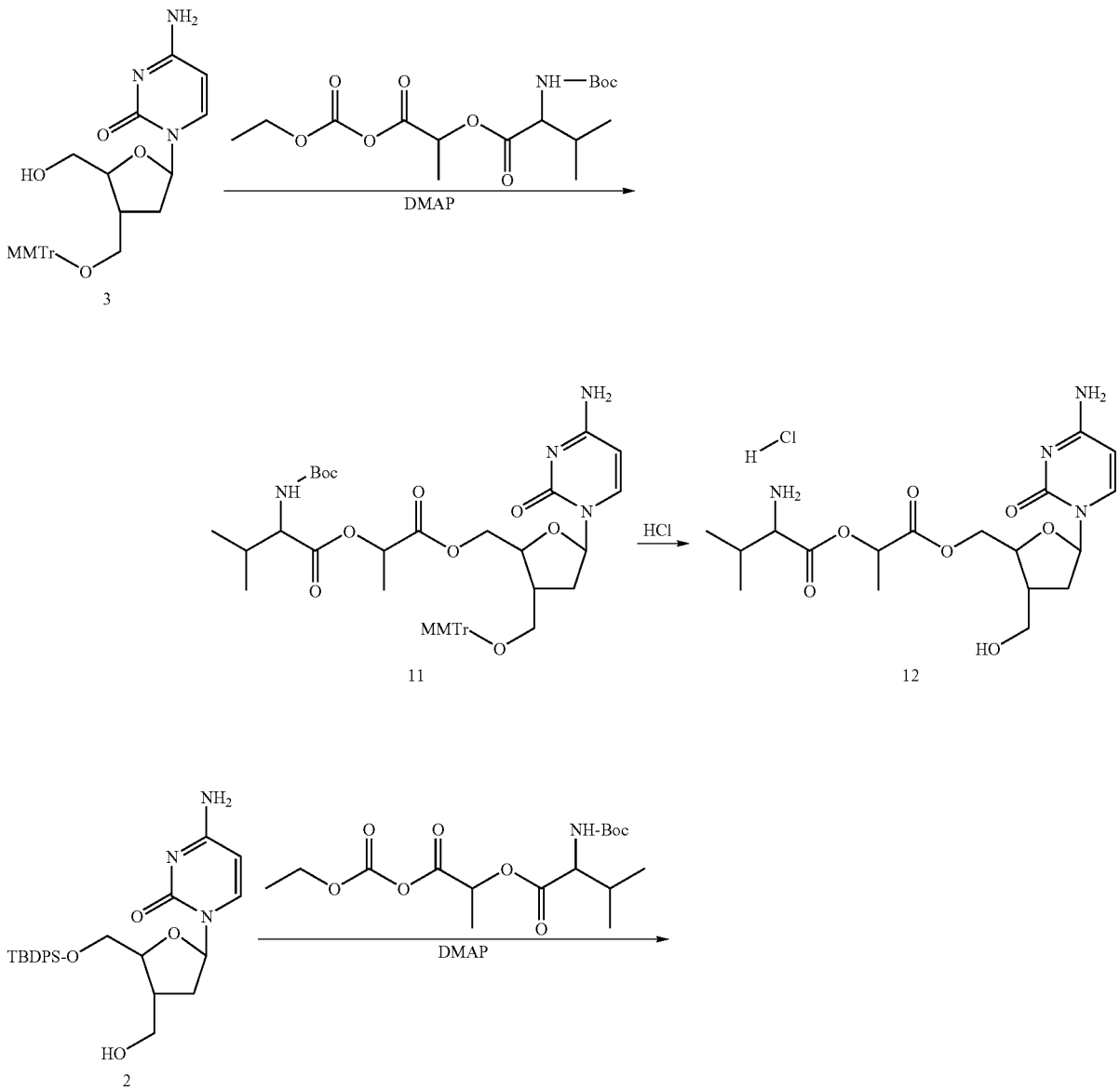

Scheme 3

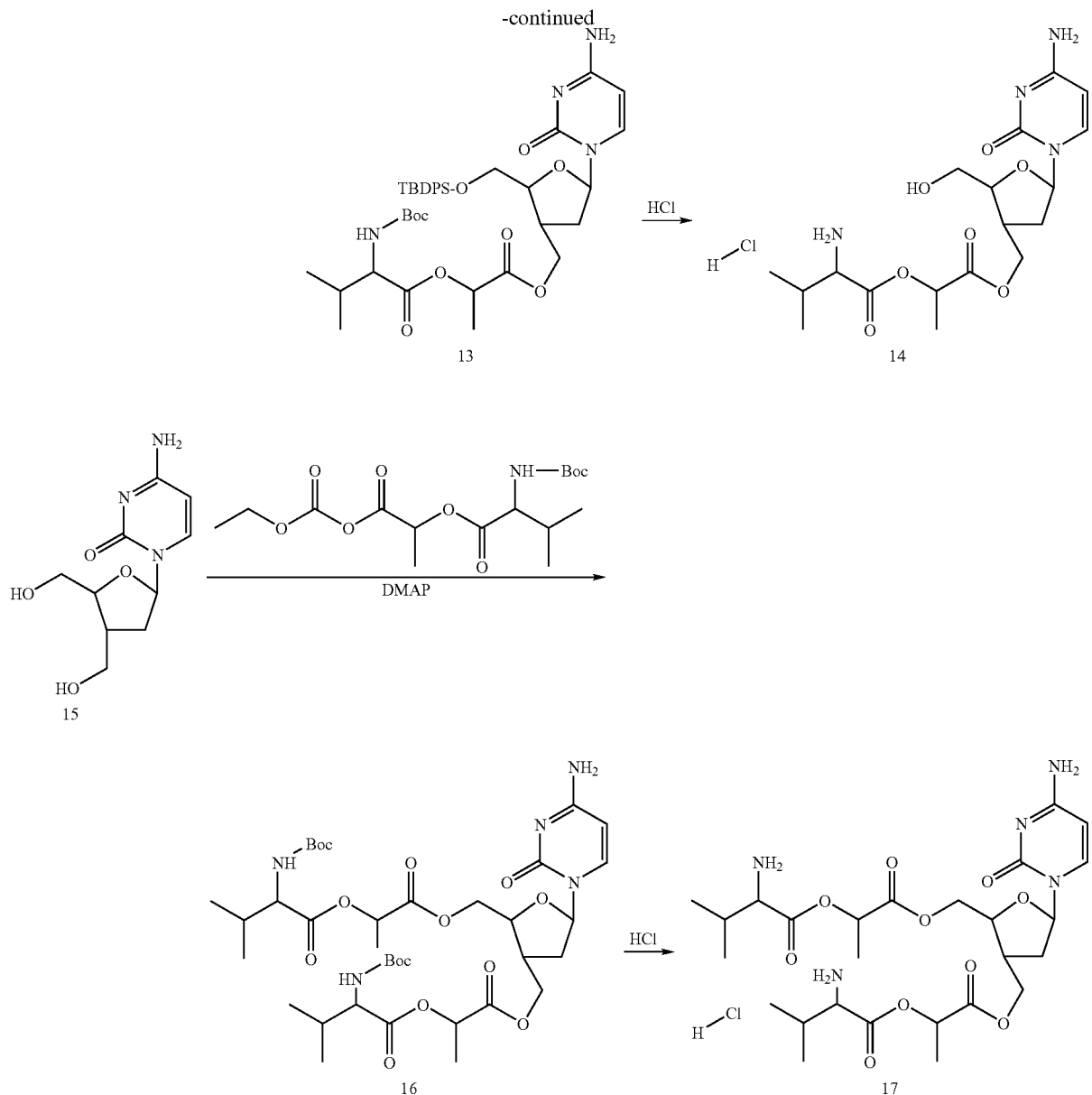

Preparation of Compound 17:

The synthesis was made from Compound 16 as for Compound 8.

Preparation of Compound 18:

Valeryl chloride (460 mg, 3.8 mmol) was added to the solution of valeric acid (390 mg, 3.8 mmol) and triethylamine (770 mg, 7.6 mmol) in THF (50 mL) at 0° C. and the mixture was stirred for 3 h, and then filtered. The filtrate was added to the solution of compound 3 (1.3 g, 2.53 mmol) and DMAP (930 mg, 7.6 mmol) in THF (50 mL). The reaction mixture was stirred overnight at room temperature. Citric acid (10%, 50 mL) was added to the mixture and it was extracted with ethyl acetate (2×50 mL). The combined organic layer was washed with citric acid (10%, 30 mL) and then with sodium carbonate (50 mL) and brine (50 mL). After drying, the organic solvent was removed and the residue was separated on silica gel column to give Compound 18 (850 mg, 56%).

Preparation of Compound 19:

Compound 18 (850 mg, 1.42 mmol) was dissolved in methanol (10 mL) and conc. HCl (1.5 mL) was added to the solution at 0° C. The reaction mixture was stirred for 0.5 h. Sodium carbonate (50 mL) was added to the mixture and it was extracted with dichloromethane (3×50 mL). Solvent was removed and the product was separated on silica gel column to give compound 19 (230 mg, 50%).

Preparation of Compound 20:

The synthesis was made from Compound 19 as for Compound 9.

Preparation of Compound 21:

The synthesis was made from Compound 20 as for Compound 8.

Preparation of Compound 22:

The synthesis was made from Compound 19 as for Compound 18.

Scheme 4
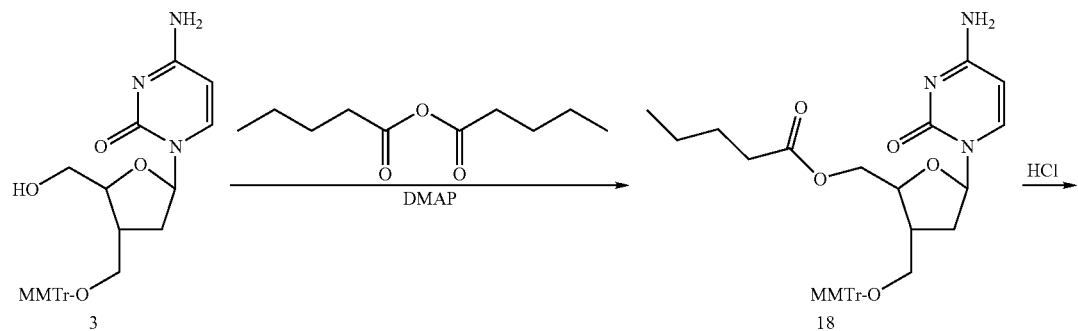
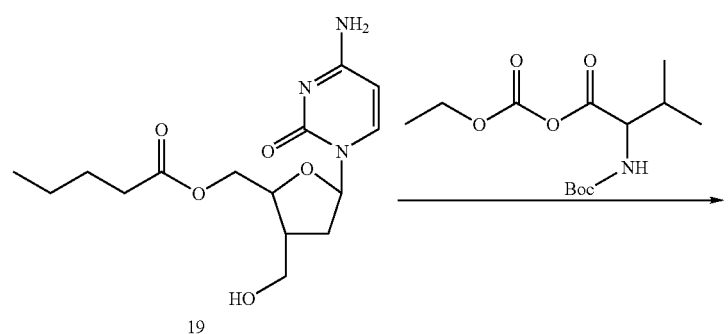
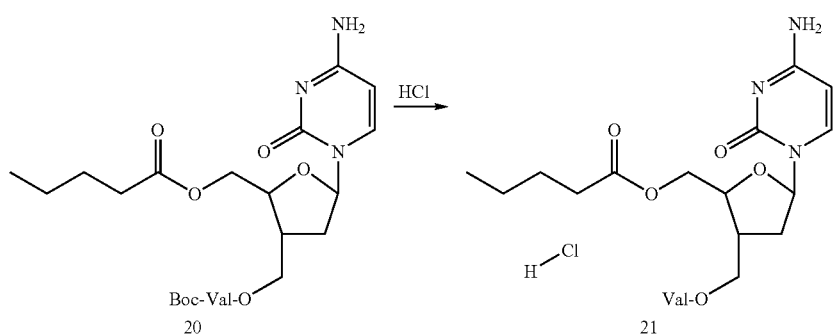
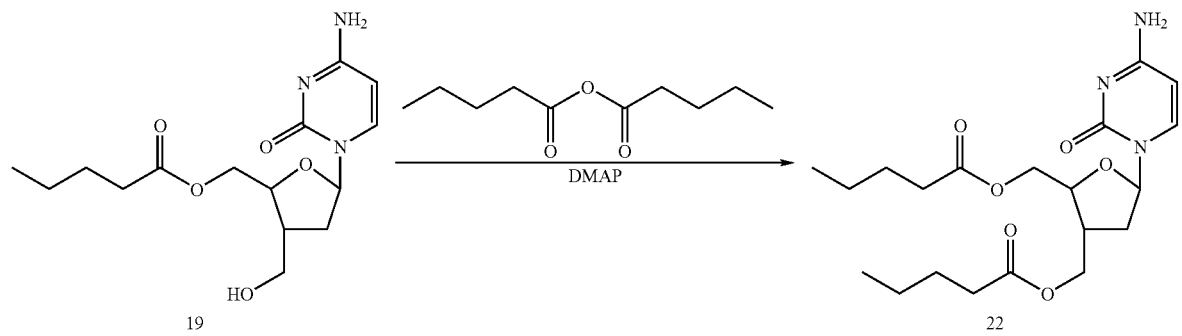

Preparation of Compound 23:

Compound 2 (1.02 g, 2.1 mmol) and DMAP (1.05 g, 8.61 mmol) were dissolved in THF (35 mL) and cooled to −78° C. Valeryl chloride (6×42 μL, 2.14 mmol) was added during 15 min. The mixture was stirred in cold temperature for 2 h and then 1 h without cooling bath. The reaction mixture was poured to 5% citric acid and then extracted with EtOAc. The combined organic layers were washed with brine, dried over $Na_2SO_4$ and evaporated to give a white solid which was purified on silica gel column with 0 to 6% MeOH in $CH_2Cl_2$ as eluent to give 0.31 g (25%) of Compound 23.

Preparation of Compound 24:

Compound 23 (0.35 g, 0.58 mmol) was dissolved in THF (20 mL), 1M TBAF in THF (0.58 mL, 0.58 mmol) was added and the mixture was stirred for 90 min at room temperature. The solvent was evaporated and the residue was purified by flash chromatography with 0 to 10% MeOH in $CH_2Cl_2$ as eluent to give 166 mg (92%) of Compound 24.

Preparation of Compound 25:

The synthesis was made from Compound 24 as for Compound 4.

Preparation of Compound 26:

The synthesis was made from Compound 25 as for Compound 8.

Example 6

Release of 2'3'-dideoxy-3'-C-hydromethylcytosine from prodrugs

Confirmation that the prodrugs of the invention convert completely to active 2'3'-dideoxy-3'-C-hydromethylcytosine parent compound can be assessed by monitoring the appearance of the parent compound in pooled human plasma, 37C, spiked with 5 uM of the prodrug:

| Compound | R | R' | Concentration of parent uM | | |
|---|---|---|---|---|---|
| | | | O min | 5 min | 20 min |
| | H | L-valyl | 0 | 0.4 | 1.0 |
| | L-valyl | H | 0.2 | 0.4 | 1.2 |
| | L-valyl | L-valyl | 0.1 | 0.2 | 0.3 |
| 12 | L-val-L-lactyl | H | 5.6 | 5.4 | 5.4 |
| 14 | H | L-val-L-lactyl | 4.6 | 4.5 | 4.6 |
| 17 | L-val-L-lactyl | L-val-L-lactyl | 3.6 | 4.2 | 4.3 |
| 19 | pentanoyl | H | 5.3 | 5.1 | 4.9 |
| 22 | pentanoyl | pentanoyl | 4.2 | 4.0 | 4.5 |
| 24 | H | pentanoyl | 3.9 | 4.2 | 4.4 |

Example 7

Bioavailability of Prodrugs

Prodrugs are typically blended in MQ grade water, 3 mg/ml and orally administered by intubation to duplicate rats. A suitable dose is 5 mg/kg. Plasma samples are taken at suitable timepoints, such as t0, 15 & 30 minutes, 1, 2, 4 and 6 hours. Recovery (as the metabolite 2',3'-dideoxy-3'-C-hydroxymethyl-β-D-erythropentofuranosylcytosine) in the plasma is measured with mass spectrometry, detected as the sodium adduct m/z 264 $(M+Na)^+$.

Results are plotted as plasma concentration against time and generally show a Cmax of the order of 3 to 5 uM. Absolute bioavailability % F is calculated in the conventional manner, ie by reference to clearance of an in vitro dose of the parent, as shown in WO97/30051.

As rats cannot be infected with HIV, the antiretroviral activity of such oral formulations cannot be directly measured, but it is noted that the $ED_{50}$ for the metabolite 2',3'-dideoxy, 3'-C-hydroxymethyl-β-D-erythropento-furanosylcytosine is typically around 0.01 uM in human H9 cells. This in turn means that peak plasma concentrations of the order of magnituted seen with these prodrugs is several hundredfold over the $ED_{50}$. Other pharmaceutical parameters such as AUC and clearance are typically consistent with achieving a 24 hour trough level well over the $ED_{50}$ with QD or BID dosing.

Each of the patent and scientific references cited in the text are listed below and are hereby incorporated by reference in their entirety.

REFERENCE

Brigitte Montes and Michel Segondy (2002) Prevalence of the mutational pattern E44D/A and/or V118I in the reverse transcriptase (RT) gene of HIV-1 in relation to treatment with nucleoside analogue RT inhibitors. J Med. Virol. 66(3):299-303.

Boyer P L, Imamichi T, Sarafianos S G, Arnold E, Hughes S H (2004) Effects of the Delta67 complex of mutations in human immunodeficiency virus type 1 reverse transcriptase on nucleoside analog excision. J. Virol. 78(18): 9987-9997.

Boyer P L, Sarafianos S G, Arnold E, Hughes S H (2002) Nucleoside analog resistance caused by insertions in the fingers of human immunodeficiency virus type 1 reverse transcriptase involves ATP-mediated excision. 76(18): 9143-9151

Girouard M, Diallo K, Marchand B, McCormick S and Gotte M (2003) Mutations E44D and V118I in the reverse transcriptase of HIV-1 play distinct mechanistic roles in dual resistance to AZT and 3TC. J Biot Chem: 5; 278(36): 34403-34410.

Harrigan, P. R., C. Stone, P. Griffin, I. Najera, S. Bloor, S. Kemp, M. Tisdale, B. Larder, and the CNA 2001 Investigative Group (2000) Resistance profile of the human immunodeficiency virus type 1 reverse transcriptase inhibitor abacavir (1592U89) after monotherapy and combination therapy. J. Infect. Dis. 181:912-920

Imamichi, T., T. Sinha, H. Imamichi, Y.-M. Zhang, J. A. Metcalf, J. Falloon, and H. C. Lane. 2000. High-level resistance to 3'-azido-3'-deoxythymidine due to a deletion in the reverse transcriptase gene of human immunodeficiency virus type 1. J. Virol. 74:1023-1028.

Imamichi, T., M. A. Murphy, H. Imamichi, and H. C. Lane. 2001. Amino acid deletion at codon 67 and Thr-to-Gly change at codon 69 of human immunodeficiency virus type 1 reverse transcriptase confer novel drug resistant profiles. J. Virol. 75:3988-3992.

Jacobo-Molina, A., J. Ding, R. G. Nanni, A. D. Clark, Jr., X. Lu, C. Tantillo, R. L. Williams, G. Kamer, A. L. Ferris, P. Clark, and E. Arnold (1993) Crystal structure of human immunodeficiency virus type 1 reverse transcriptase complexed with double-stranded DNA at 3.0 Å resolution shows bent DNA. Proc. Natl. Acad. Sci. USA 90:6320-6324

Kemp, S. D., C. Shi, S. Bloor, P. R. Harrigan, J. W. Mellors, and B. A. Larder. 1998. A novel polymorphism at codon 333 of human immunodeficiency virus type 1 reverse transcriptase can facilitate dual resistance to zidovudine and L-2',3'-dideoxy-3'-thiacytidine. J. Virol. 72:5093-5098

Larder B A, Kemp S D (1989) Multiple mutations in HIV-1 reverse transcriptase confer high-level resistance to zidovudine (AZT). Science. 1; 246(4934)1155-1158

Larder, B. A., D. Bloor, S. D. Kemp, K. Hertogs, R. L. Desmet, V. Miller, M. Stürmer, S. Staszewski, J. Ren, D. K. Stammers, D. I. Stuart, and R. Pauwels. 1999. A family of insertion mutations between codons 67 and 70 of human immunodeficiency virus type 1 reverse transcriptase confer multinucleoside analog resistance. Antimicrob Agents Chemother. 43:1961-1967

Miller, V., A. Phillips, C. Rottmann, S. Staszewski, R. Pauwels, K. Hertogs, M. P. De Béthune, S. D. Kemp, S. Bloor, P. R. Harrigan, and B. A. Larder. 1998. Dual resistance to zidovudine (ZDV) and lamivudine (3TC) in patients treated with ZDV/3TC combination therapy: association with therapy failure. J. Infect. Dis. 177:1521-1532.

Mas A., M. Parera, C. Briones, V. Soriano, M. A. Martinez, E. Domingo, and L. Menendez-Arias. 2000. Role of a dipeptide insertion between codons 69 and 70 of HIV-1 reverse transcriptase in the mechanism of AZT resistance. EMBO J. 21:5752-5761

Meyer P R, Matsuura S E, Tolun A A, Pfeifer I, So A G, Mellors J W, Scott W A (2002) Effects of specific zidovudine resistance mutations and substrate structure on nucleotide-dependent primer unblocking by human immunodeficiency virus type 1 reverse transcriptase Antimicrob Agents Chemother. 46(5):1540-1545.

Meyer P R, Lennerstrand J, Matsuura S E, Larder B A, Scott W A (2003) Effects of Dipeptide Insertions between Codons 69 and 70 of Human Immunodeficiency Virus Type 1 Reverse Transcriptase on Primer Unblocking, Deoxynucleoside Triphosphate Inhibition, and DNA Chain Elongation. J. Virol. 77(6):3871-3877

Miller, V., M. Ait-Khaled, C. Stone, P. Griffin, D. Mesogiti, A. Cutrell, R. Harrigan, S. Staszewski, C. Katlama, G. Pearce, and M. Tisdale (2000) HIV-1 reverse transcriptase (RT) genotype and susceptibility to RT inhibitors during abacavir monotherapy and combination therapy. AIDS 14:912-920

Marcelin A G, Delaugerre C, Wirden M, Viegas P, Simon A, Katlama C and Calvez V (2004) Thymidine analogue reverse transcriptase inhibitors resistance mutations profiles and association to other nucleoside reverse transcriptase inhibitors resistance mutations observed in the context of virological failure. J Med. Virol. 72(1):162-165

Martin, J. L., J. E. Wilson, R. L. Haynes, and P. A. Furman (1993) Mechanism of resistance of human immunodeficiency virus type 1 to 2',3' dideoxyinosine. Proc. Natl. Acad. Sci. USA 90:6135-6139

Mitsuya H., Yarchoan R. and Broder S. (1990) Molecular targets for AIDS therapy. Science 249: 1533-1544.

Melby T, Tortell S, Thorborn D, et al (2001) Time to appearance of NRTI-associated mutations and response to subsequent therapy for patients on failing ABC/COM. In: Program and abstracts of the 8th Conference on Retroviruses and Opportunistic Infections; Feb. 4-8, 2001; Chicago. Abstract 448

Naeger L K, Margot N A, Tuske S, Sarafianos S G, Arnold E, Miller M D (2001) Comparison of nucleoside and nucleotide reverse transcriptase inhibitor removal by the adenosine triphosphate-dependent chain-terminator removal mechanism. Presented at the 5th International Workshop on HIV Drug Resistance & Treatment Strategies Antivir Ther:6(suppl 1):39. Abstract 48.

Parikh U (a), Koontz D, Hammond J, et al. (2003) K65R: a multi-nucleoside resistance mutation of low but increasing frequency. 12th International HIV Drug Resistance Workshop: Basic Principles & Clinical Implications; Antivir Ther. 2003; 8:S152. Abstract 136.

Parikh U (b), Koontz D, Sluis-Cremer N, et al. K65R: a multinucleoside resistance mutation of increasing prevalence exhibits bi-directional phenotypic antagonism with TAM. Program and abstracts of the 11th Conference on Retroviruses and Opportunistic Infections; Feb. 8-11, 2004; San Francisco, Calif. Abstract 54

Reardon, J. E. (1993) Human immunodeficiency virus reverse transcriptase. A kinetic analysis of RNA-dependent and DNA-dependent DNA polymerization. J. Biol. Chem. 268:8743-8751

Sturmer M, Staszewski S, Doerr H W, Larder B, Bloor S, Hertogs K (2003) Correlation of Phenotypic Zidovudine Resistance with Mutational Patterns in the Reverse Transcriptase of Human Immunodeficiency Virus Type 1: Interpretation of Established Mutations and Characterization of New Polymorphisms at Codons 208, 211, and 214. Antimicrob Agents Chemother; 47(1):54-61

St. Clair, M. B., J. L. Martin, G. Tudor-Williams, M. C. Bach, C. L. Vavro, D. M. King, P. Kellam, S. D. Kemp, and B. A. Larder (1991) Resistance to ddI and sensitivity to AZT induced by a mutation in HIV-1. Science 253:1557-1559

Schinazi R F., Larder B A. And Mellors J W (2000) Mutations in retroviral gene associated with drug resistance: 2000-2001 update. Int. Antivir. News 8:65-91

Sluis-Cremer, N., D. Arion, and M. A. Parniak. (2000) Molecular mechanisms of HIV-1 resistance to nucleoside reverse transcriptase inhibitors (NRTIs). Cell. Mol. Life. Sci. 57:1408-1422

Sarafianos S G, Clark A D Jr, Das K, Tuske S, Birktoft J J, Ilankumaran P, Ramesha A R, Sayer J M, Jerina D M, Boyer P L, Hughes S H, Arnold E (2002) Structures of HIV-1 reverse transcriptase with pre- and post-translocation AZTMP-terminated DNA EMBO J. 2002 Dec. 2; 21(23):6614-24

Sarafianos S G, Clark A D Jr, Tuske S, Squire C J, Das K, Sheng D, Ilankumaran P, Ramesha A R, Kroth H, Sayer J M, Jerina D M, Boyer P L, Hughes S H, Arnold E (2003) Trapping HIV-1 reverse transcriptase before and after translocation on DNA. J Biol. Chem. 2; 278(18):16280-16288. Epub 2003 Jan 28.

Tisdale M, Alnadaf T, and Cousens D (1997) Combination of mutations in human immunodeficiency virus type 1 reverse transcriptase required for resistance to the carbocyclic nucleoside 1592U89. Antimicrob Agents Chemother. 41:10941098

Yahi N, Tamalet C, Tourres C, (1999) Mutation patterns of the reverse transcriptase and protease genes in human immunodeficiency virus type 1-infected patients undergoing combination therapy: survey of 787 sequences. *J Clin Microbiol.* 37:4099-4106

Valer L, Martin-Carbonero L, Corral A, Mendoza C D, Soriano V (2004) Predictors of selection of K65R: tenofovir use and lack of TAMs. Antivir Ther. 2004; 9:S46.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A method of treating HIV infection comprising administering to a patient in need thereof 2',3'-dideoxy-3'-C-hydroxymethylcytidine or a prodrug thereof according to the formula:

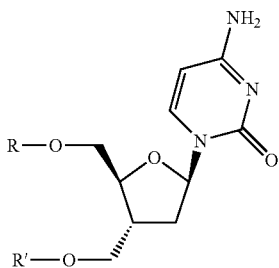

where one of R and R' is a prodrug moiety with the partial structure:

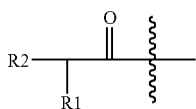

where
R$^1$ is C$_1$-C$_{18}$ straight or branched chain alkyl and R$^2$ is H; or R$^1$ is methyl and R$^2$ is NH-L-valyl or NH-L-isoleucyl; or R$^1$ is branched chain C$_3$-C$_4$ alkyl and R$_2$ is NH$_2$;
and the other one of R and R' is H or an identical prodrug moiety;
or a salt thereof, wherein the reverse transcriptase of the infecting HIV bears at least one of the following genotypic patterns:
(a) M41, ±D67, L210 and T215;
(b) D67, K70 and K219;
(c) T69S-XX; or
(d) ▲67 (deletion at 67),
which mutation allows an obligate chain terminating nucleoside- or nucleotide-phosphate to be excised from a nascent DNA strand by ATP- or pyrophosphate-mediated excision.

2. The method according to claim 1, wherein the genotypic pattern M41, ±D67, L210 and T215 comprises M41L, ±D67N, L210W and T215Y/F.

3. The method according to claim 1 or claim 2, wherein the genotypic pattern further comprises at least one additional mutation at position E44, K70, V118, H208, R211K, L214, K219 or G333.

4. The method according to claim 1 or claim 2, wherein the genetic pattern further comprises at least one additional mutation at position ▲67, T69, E203, L210, D218, H221, D223 or L228.

5. The method according to claim 1, wherein the genetic pattern D67, K70 and K219 comprises D67N, K70R and K219Q/E.

6. The method according to claim 1 or claim 5, wherein the genetic pattern D67, K70 and K219 further comprises at least one additional mutation at position M41, E44, V118, H208, R211K, L214, T215, K219 or G333.

7. The method according to claim 1 or claim 5, wherein the genetic pattern D67, K70 and K219 further comprises at least one additional mutation at position ▲67, T69, E203, L210, D218, H221, D223 or L228.

8. The method according to claim 1, wherein the genetic pattern T69S-XX further comprises at least one additional mutation at position M41, E44, D67, K70, V118, H208, L210, R211K, L214, T215, K219 or G333.

9. The method according to claim 1, wherein the genetic pattern T69S-XX further comprises at least one additional mutation at position ▲67, T69, E203, L210, D218, H221, D223 or L228.

10. The method according to claim 1, wherein the genetic pattern ▲67 further comprises at least one additional mutation at position M41, E44, D67, K70, V118, H208, L210, R211K, L214, T215, K219 or G333.

11. The method according to claim 1, wherein the genetic pattern ▲67 further comprises at least one additional mutation at position T69, T69S+XX, E203, L210, D218, H221, D223, or L228.

12. The method according to any one of claim 1, claim 2 or claim 5 wherein the reverse transcriptase further bears at least one discriminative mutation at position K65 or L74 or M184 or Q151.

13. The method according to claim 12, wherein the discriminant mutation is K65R or L74V or M184V or Q151M.

14. The method according to claim 12 wherein the discriminant mutation further comprises at least one additional mutation at position A62, V75, F77, Y115 or F116.

15. The method according to claim 1, wherein 5'-(2',3'-dideoxy-3'-C-hydroxymethylcytidine)monophosphate is incorporated into the nascent DNA chain whereby one residue selected from natural nucleotides, nucleoside analogue monophosphates (including 5'-(2',3'-dideoxy-3'-C-hydroxymethylcytidine)monophosphate) and nucleotide analogue phosphates is covalently attached to the incorporated 5'-(2',3'-dideoxy-3'-C-hydroxymethylcytidine)monophosphate, thereby inducing chain termination.

16. The method according to claim 1, wherein the compound is 2',3'-dideoxy-3'-C-hydroxymethylcytidine, or a pharmaceutically acceptable salt thereof.

17. The method according to claim 1, wherein one or both of R and R' are
L-valyl-L-lactyl-, L-valyl- or C$_1$-C$_6$ alkanoyl-.

18. The method according to claim 17, wherein the compound is denoted:
5'-O-[2-S-(L-valyloxy)-propionyl]-2'-3'-dideoxy-3-C-hydroxymethylcytidine,
2',3'-dideoxy-3'-C-[2-S-(L-valyloxy)-propionyl]-oxymethylcytidine;
5'-O-pentanoyl-2'-3'-dideoxy 3-C-hydroxymethylcytosine;,
2',3'-dideoxy-3'-C-pentanoyl-oxymethylcytidine; or
5'-O-pentanoyl-2'-3'-dideoxy-3-C-pentanoyl-oxymethylcytidine;
or a pharmaceutically acceptable salt thereof.

19. The method according to claim 1, wherein the 2',3'-dideoxy-3'-C-hydroxymethylcytidine is administered in the range 0.05-0.5 mg/kg/day.

20. The method according to claim 19, wherein the 2',3'-dideoxy-3'-C-hydroxymethylcytidine is administered at less than 0.1 mg/kg/day.

* * * * *